US009289574B2

(12) United States Patent
Maxik et al.

(10) Patent No.: US 9,289,574 B2
(45) Date of Patent: Mar. 22, 2016

(54) THREE-CHANNEL TUNED LED LAMP FOR PRODUCING BIOLOGICALLY-ADJUSTED LIGHT

(71) Applicant: Biological Illumination, LLC, Satellite Beach, FL (US)

(72) Inventors: Fredric S. Maxik, Cocoa Beach, FL (US); David E. Bartine, Cocoa, FL (US); Robert R. Soler, Cocoa Beach, FL (US); Eliza Katar Grove, Satellite Beach, FL (US); Eric Bretschneider, Bowling Green, KY (US)

(73) Assignee: Biological Illumination, LLC, Melbourne, FL (US)

( * ) Notice: Subject to any disclaimer, the term of this patent is extended or adjusted under 35 U.S.C. 154(b) by 0 days.

(21) Appl. No.: 14/514,010

(22) Filed: Oct. 14, 2014

(65) Prior Publication Data

US 2015/0054415 A1    Feb. 26, 2015

Related U.S. Application Data

(63) Continuation-in-part of application No. 14/165,198, filed on Jan. 27, 2014, now Pat. No. 8,941,329, which is a continuation of application No. 13/311,300, filed on Dec. 5, 2011, now Pat. No. 8,686,641.

(51) Int. Cl.
*H01L 27/15* (2006.01)
*H05B 37/02* (2006.01)
(Continued)

(52) U.S. Cl.
CPC ............... *A61M 21/02* (2013.01); *A61M 21/00* (2013.01); *A61N 5/0618* (2013.01); *F21K 9/13* (2013.01);
(Continued)

(58) Field of Classification Search
CPC ..... H05B 37/02; H05B 33/086; H01L 27/153
USPC .................... 315/192, 294; 362/249.02, 231
See application file for complete search history.

(56) References Cited

U.S. PATENT DOCUMENTS 5,046,494 A    9/1991   Searfoss et al.
5,221,877 A    6/1993   Falk
(Continued)

FOREIGN PATENT DOCUMENTS

CN    101 702 421 A    5/2010
EP         0851260      7/1998
(Continued)

OTHER PUBLICATIONS

Arthur P. Fraas, Heat Exchanger Design, 1989, p. 60, John Wiley & Sons, Inc., Canada.
(Continued)

*Primary Examiner* — Daniel D Chang
(74) *Attorney, Agent, or Firm* — Mark Malek; Daniel Pierron; Widerman Malek, PL

(57) ABSTRACT

An LED lamp comprising a housing, a drive circuit, and a plurality of LED dies driven by the drive circuit, The plurality of LED dies may be in a ratio of at least one of 15 mint LED dies to 5 hyper red LED dies to 4 blue LED dies and 1 mint LED die to 1 hyper red LED die to 1 blue LED die. The drive circuit may operate the LED dies such that a relative peak intensity of the blue LED dies is within the range from 80%-90% or 90%-100% of a peak intensity of the hyper red LED dies, and a relative peak intensity of the mint LED dies is within the range of 50%-60% or 30%-40% of the peak intensity of the hyper red LED dies.

20 Claims, 16 Drawing Sheets

(51) Int. Cl.
*A61M 21/02* (2006.01)
*H05B 33/08* (2006.01)
*F21K 99/00* (2010.01)
*A61M 21/00* (2006.01)
*A61N 5/06* (2006.01)
*F21Y 101/02* (2006.01)
*F21Y 113/00* (2006.01)

(52) U.S. Cl.
CPC .......... *H05B 33/086* (2013.01); *H05B 33/0863* (2013.01); *H05B 33/0872* (2013.01); *A61M 2021/0005* (2013.01); *A61M 2021/0044* (2013.01); *A61M 2021/0083* (2013.01); *A61N 2005/0651* (2013.01); *A61N 2005/0652* (2013.01); *A61N 2005/0663* (2013.01); *F21K 9/1355* (2013.01); *F21Y 2101/02* (2013.01); *F21Y 2113/005* (2013.01)

(56) References Cited

U.S. PATENT DOCUMENTS

| | | |
|---|---|---|
| 5,523,878 A | 6/1996 | Wallace et al. |
| 5,680,230 A | 10/1997 | Kaburagi et al. |
| 5,704,701 A | 1/1998 | Kavanagh et al. |
| 5,813,753 A | 9/1998 | Vriens et al. |
| 5,997,150 A | 12/1999 | Anderson |
| 6,027,225 A | 2/2000 | Martin et al. |
| 6,140,646 A | 10/2000 | Busta et al. |
| 6,259,572 B1 | 7/2001 | Meyer, Jr. |
| 6,290,382 B1 | 9/2001 | Bourn et al. |
| 6,341,876 B1 | 1/2002 | Moss et al. |
| 6,356,700 B1 | 3/2002 | Strobl |
| 6,369,517 B2 | 4/2002 | Song et al. |
| 6,370,168 B1 | 4/2002 | Spinelli |
| 6,459,919 B1 | 10/2002 | Lys et al. |
| 6,528,954 B1 | 3/2003 | Lys et al. |
| 6,542,671 B1 | 4/2003 | Ma et al. |
| 6,561,656 B1 | 5/2003 | Kojima et al. |
| 6,577,080 B2 | 6/2003 | Lys et al. |
| 6,586,882 B1 | 7/2003 | Harbers |
| 6,594,090 B2 | 7/2003 | Kruschwitz et al. |
| 6,641,283 B1 | 11/2003 | Bohler |
| 6,733,135 B2 | 5/2004 | Dho |
| 6,734,639 B2 | 5/2004 | Chang et al. |
| 6,762,562 B2 | 7/2004 | Leong |
| 6,767,111 B1 | 7/2004 | Lai |
| 6,787,999 B2 | 9/2004 | Stimac et al. |
| 6,817,735 B2 | 11/2004 | Shimizu et al. |
| 6,870,523 B1 | 3/2005 | Ben-David et al. |
| 6,871,982 B2 | 3/2005 | Holman et al. |
| 6,893,140 B2 | 5/2005 | Storey et al. |
| 6,940,101 B2 | 9/2005 | Yano et al. |
| 6,945,672 B2 | 9/2005 | Du et al. |
| 6,967,761 B2 | 11/2005 | Starkweather et al. |
| 6,974,713 B2 | 12/2005 | Patel et al. |
| 7,008,559 B2 | 3/2006 | Chen |
| 7,015,636 B2 | 3/2006 | Bolta |
| 7,034,934 B2 | 4/2006 | Manning |
| 7,042,623 B1 | 5/2006 | Huibers et al. |
| 7,058,197 B1 | 6/2006 | McGuire et al. |
| 7,070,281 B2 | 7/2006 | Kato |
| 7,072,096 B2 | 7/2006 | Holman et al. |
| 7,075,707 B1 | 7/2006 | Rapaport et al. |
| 7,083,304 B2 | 8/2006 | Rhoads |
| 7,095,053 B2 | 8/2006 | Mazzochette et al. |
| 7,144,131 B2 | 12/2006 | Rains |
| 7,157,745 B2 | 1/2007 | Blonder et al. |
| 7,178,941 B2 | 2/2007 | Roberge et al. |
| 7,184,201 B2 | 2/2007 | Duncan |
| 7,187,484 B2 | 3/2007 | Mehrl |
| 7,213,926 B2 | 5/2007 | May et al. |
| 7,234,844 B2 | 6/2007 | Bolta et al. |
| 7,246,923 B2 | 7/2007 | Conner |
| 7,247,874 B2 | 7/2007 | Bode et al. |
| 7,252,408 B2 | 8/2007 | Mazzochette et al. |
| 7,255,469 B2 | 8/2007 | Wheatley et al. |
| 7,261,453 B2 | 8/2007 | Morejon et al. |
| 7,289,090 B2 | 10/2007 | Morgan |
| 7,300,177 B2 | 11/2007 | Conner |
| 7,303,291 B2 | 12/2007 | Ikeda et al. |
| 7,306,352 B2 | 12/2007 | Sokolov et al. |
| 7,319,293 B2 | 1/2008 | Maxik |
| 7,324,076 B2 | 1/2008 | Lee et al. |
| 7,325,956 B2 | 2/2008 | Morejon et al. |
| 7,342,658 B2 | 3/2008 | Kowarz et al. |
| 7,344,279 B2 | 3/2008 | Mueller et al. |
| 7,344,280 B2 | 3/2008 | Panagotacos et al. |
| 7,349,095 B2 | 3/2008 | Kurosaki |
| 7,353,859 B2 | 4/2008 | Stevanovic et al. |
| 7,369,056 B2 | 5/2008 | McCollough et al. |
| 7,382,091 B2 | 6/2008 | Chen et al. |
| 7,382,632 B2 | 6/2008 | Alo et al. |
| 7,400,439 B2 | 7/2008 | Holman |
| 7,427,146 B2 | 9/2008 | Conner |
| 7,429,983 B2 | 9/2008 | Islam |
| 7,434,946 B2 | 10/2008 | Huibers |
| 7,436,996 B2 | 10/2008 | Ben-Chorin |
| 7,438,443 B2 | 10/2008 | Tatsuno et al. |
| 7,476,016 B2 | 1/2009 | Kurihara |
| 7,479,861 B2 | 1/2009 | Zepke et al. |
| 7,497,596 B2 | 3/2009 | Ge |
| 7,520,607 B2 | 4/2009 | Casper et al. |
| 7,520,642 B2 | 4/2009 | Holman et al. |
| 7,521,875 B2 | 4/2009 | Maxik |
| 7,528,421 B2 | 5/2009 | Mazzochette |
| 7,530,708 B2 | 5/2009 | Park |
| 7,537,347 B2 | 5/2009 | Dewald |
| 7,540,616 B2 | 6/2009 | Conner |
| 7,556,376 B2 | 7/2009 | Ishak et al. |
| 7,556,406 B2 | 7/2009 | Petroski et al. |
| 7,573,210 B2 | 8/2009 | Ashdown et al. |
| 7,598,686 B2 | 10/2009 | Lys et al. |
| 7,598,961 B2 | 10/2009 | Higgins |
| 7,605,971 B2 | 10/2009 | Ishii et al. |
| 7,619,372 B2 | 11/2009 | Garrity |
| 7,626,755 B2 | 12/2009 | Furuya et al. |
| 7,633,093 B2 | 12/2009 | Blonder et al. |
| 7,633,779 B2 | 12/2009 | Garrity et al. |
| 7,637,643 B2 | 12/2009 | Maxik |
| 7,670,021 B2 | 3/2010 | Chou |
| 7,677,736 B2 | 3/2010 | Kazasumi et al. |
| 7,678,140 B2 | 3/2010 | Brainard et al. |
| 7,679,281 B2 | 3/2010 | Kim et al. |
| 7,684,007 B2 | 3/2010 | Hull et al. |
| 7,703,943 B2 | 4/2010 | Li et al. |
| 7,705,810 B2 | 4/2010 | Choi et al. |
| 7,708,452 B2 | 5/2010 | Maxik et al. |
| 7,709,811 B2 | 5/2010 | Conner |
| 7,719,766 B2 | 5/2010 | Grasser et al. |
| 7,728,846 B2 | 6/2010 | Higgins et al. |
| 7,732,825 B2 | 6/2010 | Kim et al. |
| 7,748,845 B2 | 7/2010 | Casper et al. |
| 7,748,877 B1 | 7/2010 | Colby |
| 7,766,490 B2 | 8/2010 | Harbers et al. |
| 7,806,575 B2 | 10/2010 | Willwohl et al. |
| 7,819,556 B2 | 10/2010 | Heffington et al. |
| 7,824,075 B2 | 11/2010 | Maxik et al. |
| 7,828,453 B2 | 11/2010 | Tran et al. |
| 7,828,465 B2 | 11/2010 | Roberge et al. |
| 7,832,878 B2 | 11/2010 | Brukilacchio et al. |
| 7,834,867 B2 | 11/2010 | Sprague et al. |
| 7,835,056 B2 | 11/2010 | Doucet et al. |
| 7,841,714 B2 | 11/2010 | Grueber |
| 7,845,823 B2 | 12/2010 | Mueller et al. |
| 7,855,376 B2 | 12/2010 | Cantin et al. |
| 7,871,839 B2 | 1/2011 | Lee |
| 7,880,400 B2 | 2/2011 | Zhoo et al. |
| 7,889,430 B2 | 2/2011 | El-Ghoroury et al. |
| 7,905,637 B2 | 3/2011 | Caluori et al. |
| 7,906,722 B2 | 3/2011 | Fork et al. |
| 7,906,789 B2 | 3/2011 | Jung et al. |
| 7,922,356 B2 | 4/2011 | Maxik et al. |
| 7,928,565 B2 | 4/2011 | Brunschwiler et al. |

(56) References Cited

U.S. PATENT DOCUMENTS

| | | |
|---|---|---|
| 7,964,883 B2 | 6/2011 | Mazzochete et al. |
| 7,972,030 B2 | 7/2011 | Li |
| 7,976,182 B2 | 7/2011 | Ribarich |
| 7,976,205 B2 | 7/2011 | Grotsch et al. |
| 7,984,989 B2 | 7/2011 | Gruber |
| 8,016,443 B2 | 9/2011 | Falicoff et al. |
| 8,038,314 B2 | 10/2011 | Ladewig |
| 8,040,070 B2 | 10/2011 | Myers et al. |
| 8,047,660 B2 | 11/2011 | Penn et al. |
| 8,049,763 B2 | 11/2011 | Kwak et al. |
| 8,061,857 B2 | 11/2011 | Liu et al. |
| 8,070,302 B2 | 12/2011 | Hatanaka et al. |
| 8,076,680 B2 | 12/2011 | Lee et al. |
| 8,083,364 B2 | 12/2011 | Allen |
| 8,096,668 B2 | 1/2012 | Abu-Ageel |
| 8,115,419 B2 | 2/2012 | Given et al. |
| 8,164,844 B2 | 4/2012 | Toda et al. |
| 8,172,436 B2 | 5/2012 | Coleman et al. |
| 8,182,106 B2 | 5/2012 | Shin et al. |
| 8,182,115 B2 | 5/2012 | Takahashi et al. |
| 8,188,687 B2 | 5/2012 | Lee et al. |
| 8,192,047 B2 | 6/2012 | Bailey et al. |
| 8,201,968 B2 | 6/2012 | Maxik et al. |
| 8,207,676 B2 | 6/2012 | Hilgers |
| 8,212,836 B2 | 7/2012 | Matsumoto et al. |
| 8,227,813 B2 | 7/2012 | Ward |
| 8,253,336 B2 | 8/2012 | Maxik et al. |
| 8,256,921 B2 | 9/2012 | Crookham et al. |
| 8,272,763 B1 | 9/2012 | Chinnam et al. |
| 8,274,089 B2 | 9/2012 | Lee |
| 8,297,783 B2 | 10/2012 | Kim |
| 8,297,798 B1 | 10/2012 | Pittman et al. |
| 8,304,978 B2 | 11/2012 | Kim et al. |
| 8,310,171 B2 | 11/2012 | Reisenauer et al. |
| 8,319,445 B2 | 11/2012 | McKinney et al. |
| 8,324,808 B2 | 12/2012 | Maxik et al. |
| 8,324,823 B2 | 12/2012 | Choi et al. |
| 8,324,840 B2 | 12/2012 | Shteynberg et al. |
| 8,331,099 B2 | 12/2012 | Geissler et al. |
| 8,337,029 B2 | 12/2012 | Li |
| 8,348,492 B2 | 1/2013 | Mier-Langner et al. |
| 8,378,574 B2 | 2/2013 | Schlangen et al. |
| 8,384,984 B2 | 2/2013 | Maxik et al. |
| 8,401,231 B2 | 3/2013 | Maxik et al. |
| 8,405,299 B2 | 3/2013 | Toda et al. |
| 8,410,717 B2 | 4/2013 | Shteynberg et al. |
| 8,410,725 B2 | 4/2013 | Jacobs et al. |
| 8,427,590 B2 | 4/2013 | Raring et al. |
| 8,441,210 B2 | 5/2013 | Shteynberg et al. |
| 8,446,095 B2 | 5/2013 | Maxik et al. |
| 8,454,197 B2 | 6/2013 | Hauschulte |
| 8,465,167 B2 | 6/2013 | Maxik et al. |
| 8,531,126 B2 | 9/2013 | Kaihotsu et al. |
| 8,547,391 B2 | 10/2013 | Maxik et al. |
| 8,643,276 B2 | 2/2014 | Maxik et al. |
| 8,672,518 B2 | 3/2014 | Boomgaarden et al. |
| 8,674,613 B2 | 3/2014 | Gray et al. |
| 8,678,787 B2 | 3/2014 | Hirata et al. |
| 8,680,457 B2 | 3/2014 | Maxik et al. |
| 8,686,641 B2 | 4/2014 | Maxik et al. |
| 8,928,023 B1 * | 1/2015 | Coleiny et al. ............... 257/98 |
| 2002/0113555 A1 | 8/2002 | Lys et al. |
| 2002/0151941 A1 | 10/2002 | Okawa et al. |
| 2004/0052076 A1 | 3/2004 | Mueller et al. |
| 2005/0033119 A1 | 2/2005 | Okawa et al. |
| 2005/0218780 A1 | 10/2005 | Chen |
| 2005/0267213 A1 | 12/2005 | Gold et al. |
| 2006/0002108 A1 | 1/2006 | Ouderkirk et al. |
| 2006/0002110 A1 | 1/2006 | Dowling et al. |
| 2006/0164005 A1 | 7/2006 | Sun |
| 2006/0285193 A1 | 12/2006 | Kimura et al. |
| 2007/0013871 A1 | 1/2007 | Marshall et al. |
| 2007/0041167 A1 | 2/2007 | Nachi |
| 2007/0159492 A1 | 7/2007 | Lo et al. |
| 2007/0165193 A1 | 7/2007 | Kubo et al. |
| 2007/0262714 A1 | 11/2007 | Bylsma |
| 2008/0119912 A1 | 5/2008 | Hayes |
| 2008/0143973 A1 | 6/2008 | Wu |
| 2008/0170398 A1 | 7/2008 | Kim |
| 2008/0198572 A1 | 8/2008 | Medendorp |
| 2008/0232084 A1 | 9/2008 | Kon |
| 2008/0232116 A1 | 9/2008 | Kim |
| 2009/0027900 A1 | 1/2009 | Janos et al. |
| 2009/0036952 A1 | 2/2009 | Kao et al. |
| 2009/0059585 A1 | 3/2009 | Chen et al. |
| 2009/0128781 A1 | 5/2009 | Li |
| 2009/0141506 A1 | 6/2009 | Lan et al. |
| 2009/0175041 A1 | 7/2009 | Yuen et al. |
| 2009/0273931 A1 | 11/2009 | Ito et al. |
| 2009/0303694 A1 | 12/2009 | Roth et al. |
| 2010/0001652 A1 | 1/2010 | Damsleth |
| 2010/0006762 A1 | 1/2010 | Yoshida et al. |
| 2010/0051976 A1 | 3/2010 | Rooymans |
| 2010/0053959 A1 | 3/2010 | Ijzerman et al. |
| 2010/0076250 A1 | 3/2010 | Van Woudenberg et al. |
| 2010/0096993 A1 | 4/2010 | Ashdown et al. |
| 2010/0103389 A1 | 4/2010 | McVea et al. |
| 2010/0121420 A1 | 5/2010 | Fiset et al. |
| 2010/0202129 A1 | 8/2010 | Abu-Ageel |
| 2010/0244700 A1 | 9/2010 | Chong et al. |
| 2010/0244735 A1 | 9/2010 | Buelow |
| 2010/0244740 A1 | 9/2010 | Alpert et al. |
| 2010/0270942 A1 | 10/2010 | Hui et al. |
| 2010/0277084 A1 | 11/2010 | Lee et al. |
| 2010/0315320 A1 | 12/2010 | Yoshida |
| 2010/0321641 A1 | 12/2010 | Van Der Lubbe |
| 2011/0012137 A1 | 1/2011 | Lin et al. |
| 2011/0080635 A1 | 4/2011 | Takeuchi |
| 2011/0115381 A1 | 5/2011 | Carlin |
| 2011/0205738 A1 | 8/2011 | Peifer et al. |
| 2011/0299277 A1 | 12/2011 | Ehara |
| 2011/0310446 A1 | 12/2011 | Komatsu |
| 2012/0002411 A1 | 1/2012 | Ladewig |
| 2012/0051041 A1 | 3/2012 | Edmond et al. |
| 2012/0106144 A1 | 5/2012 | Chang |
| 2012/0140440 A1 | 6/2012 | Dam et al. |
| 2012/0140461 A1 | 6/2012 | Pickard et al. |
| 2012/0188769 A1 | 7/2012 | Lau |
| 2012/0201034 A1 | 8/2012 | Li |
| 2012/0262902 A1 | 10/2012 | Pickard et al. |
| 2012/0327650 A1 | 12/2012 | Lay et al. |
| 2013/0021792 A1 | 1/2013 | Snell et al. |
| 2013/0021803 A1 | 1/2013 | Pickard et al. |
| 2013/0088142 A1 * | 4/2013 | Allen ............................ 313/498 |
| 2013/0099696 A1 | 4/2013 | Maxik et al. |
| 2013/0120963 A1 | 5/2013 | Holland et al. |
| 2013/0223055 A1 | 8/2013 | Holland et al. |
| 2013/0278148 A1 | 10/2013 | Maxik et al. |
| 2013/0278172 A1 | 10/2013 | Maxik et al. |
| 2013/0293148 A1 | 11/2013 | Holland et al. |
| 2014/0015438 A1 | 1/2014 | Maxik et al. |
| 2014/0049191 A1 | 2/2014 | Maxik et al. |
| 2014/0049192 A1 | 2/2014 | Maxik et al. |

FOREIGN PATENT DOCUMENTS

| | | |
|---|---|---|
| EP | 1 888 708 | 2/2008 |
| EP | 1950491 | 7/2008 |
| EP | 2 094 064 A1 | 8/2009 |
| EP | 2 199 657 | 6/2010 |
| EP | 2 242 335 | 10/2010 |
| JP | 2005534155 | 11/2005 |
| JP | 2008226567 | 9/2008 |
| WO | WO03098977 | 11/2003 |
| WO | WO2008137732 | 11/2008 |
| WO | WO2009029575 | 3/2009 |
| WO | WO2009121539 A1 | 10/2009 |
| WO | WO2012064470 | 5/2012 |

(56) References Cited

FOREIGN PATENT DOCUMENTS

| WO | WO2012135173 | 10/2012 |
|---|---|---|
| WO | WO2012158665 | 11/2012 |

OTHER PUBLICATIONS

Binnie et al. (1979) "Fluorescent Lighting and Epilepsy" Epilepsia 20(6):725-727.
Charamisinau et al. (2005) "Semiconductor laser insert with Uniform Illumination for Use in Photodynamic Therapy" Appl Opt 44(24):5055-5068.
EP International Search Report for Application No. 10174449.8; (Dec. 14, 2010).
ERBA Shedding Light on Photosensitivity, One of Epilepsy's Most Complex Conditions. Photosensitivity and Epilepsy. Epilepsy Foundation. Accessed: Aug. 28, 2009. http://www.epilepsyfoundation.org/aboutepilepsy/seizures/photosensitivity-/gerba.cfm.
Figueiro et al. (2004) "Spectral Sensitivity of the Circadian System" Proc. SPIE 5187:207.
Figueiro et al. (2008) "Retinal Mechanisms Determine the Subadditive Response to Polychromatic Light by the Human Circadian System" Neurosci Lett 438(2):242.
Gabrecht et al. (2007) "Design of a Light Delivery System for the Photodynamic Treatment of the Crohn's Disease" Proc. SPIE 6632:1-9.
H. A El-Shaikh, S. V. Garimella, "Enhancement of Air Jet Impingement Heat Transfer using Pin-Fin Heat Sinks", D IEEE Transactions on Components and Packaging Technology, Jun. 2000, vol. 23, No. 2.
Happawana et al. (2009) "Direct De-Ionized Water-Cooled Semiconductor Laser Package for Photodynamic Therapy of Esophageal Carcinoma: Design and Analysis" J Electron Pack 131(2):1-7.
Harding & Harding (1999) "Televised Material and Photosensitive Epilepsy" Epilepsia 40(Suppl. 4):65.
Jones, Eric D., Light Emitting Diodes (LEDS) for General Lumination, an Optoelectronics Industry Development Association (OIDA) Technology Roadmap, OIDA Report, Mar. 2001, published by OIDA in Washington D.C.
J. Y. San, C. H. Huang, M. H, Shu, "Impingement cooling of a confined circular air jet", In t. J. Heat Mass Transf., 1997. pp. 1355-1364, vol. 40.
Kuller & Laike (1998) "The Impact of Flicker from Fluorescent Lighting on Well-Being, Perfiormance and Physiological Arousal" Ergonomics 41(4):433-447.
Lakatos (2006) "Recent trends in the epidemiology of Inflammatory Bowel Disease: Up or Down?" World J Gastroenterol 12(38):6102.
N. T. Obot, W. J. Douglas, A S. Mujumdar, "Effect of Semi-confinement on Impingement Heat Transfer", Proc. 7th Int. Heat Transf. Conf., 1982, pp. 1355-1364. vol. 3.
Ortner & Dorta (2006) "Technology Insight: Photodynamic Therapy for Cholangiocarcinoma" Nat Clin Pract Gastroenterol Hepatol 3(8):459-467.
Rea (2010) "Circadian Light" J Circadian Rhythms 8(1):2.
Rea et al. (2010) "The Potential of Outdoor Lighting for Stimulating the Human Circadian System" Alliance for Solid-State Illumination Systems and Technologies (ASSIST), May 13, 2010, p. 1-11.
Rosco Laboratories Poster "Color Filter Technical Data Sheet: #87 Pale Yellow Green" (2001).
S. A Solovitz, L. D. Stevanovic, R. A Beaupre, "Microchannels Take Heatsinks to the Next Level", Power Electronics Technology, Nov. 2006.
Sengupta, Upal, "How to Implement A 5-W Wireless Power System", How2Power Today, pp. 1-8, (Jul. 2010).
Stevens (1987) "Electronic Power Use and Breast Cancer: A Hypothesis" Am J Epidemiol 125(4):556-561.
Tannith Cattermole, "Smart Energy Glass controls light on demand", Gizmag.com, Apr. 18, 2010 accessed Nov. 1, 2011.
Topalkara et al. (1998) "Effects of flash frequency and repetition of intermittent photic stimulation on photoparoxysmal responses" Seizure 7(13):249-253.
Veitch & McColl (1995) "Modulation of Fluorescent Light: Flicker Rate and Light Source Effects on Visual Performance and Visual Comfort" Lighting Research and Technology 27:243-256.
Wang (2005) "The Critical Role of Light in Promoting Intestinal Inflammation and Crohn's Disease" J Immunol 174 (12):8173-8182.
Wilkins et al. (1979) "Neurophysical aspects of pattern-sensitive epilepsy" Brain 102:1-25.
Wilkins et al. (1989) "Fluorescent lighting, headaches, and eyestrain" Lighting Res Technol 21(1):11-18.
Yongmann M. Chung, Kai H. Luo, "Unsteady Heat Transfer Analysis of an Impinging Jet", Journal of Heat Transfer—Transactions of the ASME, Dec. 2002, pp. 1039-1048, vol. 124, No. 6.
U.S. Patent and Trademark Office's Non-Final Office Action dated May 23, 2013 cited in related U.S. Appl. No. 13/311,300 (14 pages).
U.S. Patent and Trademark Office's Applicant-Initiated Interview Summary dated Jul. 8, 2013 cited in related U.S. Appl. No. 13/311,300 (5 pages).
U.S. Patent and Trademark Office's Final Office Action dated Aug. 29, 2013 cited in related U.S. Appl. No. 13/311,300 (10 pages).
U.S. Patent and Trademark Office's Applicant-Initiated Interview Summary dated Oct. 30, 2013 cited in related U.S. Appl. No. 13/311,300 (3 pages).
PCT International Search Report from the International Searching Authority, dated Oct. 21, 2013 cited in related PCT/US2012/067816 (5 pages).
PCT Written Opinion from the International Searching Authority, dated Oct. 21, 2013 cited in related PCT/US2012/067816 (8 pages).

\* cited by examiner

FIG. 10A

THREE-CHANNEL TUNED LED LAMP FOR PRODUCING BIOLOGICALLY-ADJUSTED LIGHT

RELATED APPLICATIONS

This application is a continuation-in-part and claims the benefit under 35 U.S.C. §120 of U.S. patent application Ser. No. 14/165,198 titled Tunable LED Lamp for Producing Biologically-Adjusted Light filed Jan. 27, 2014, which is in turn a continuation of U.S. patent application Ser. No. 13/311,300, now U.S. Pat. No. 8,686,641, titled Tunable LED Lamp for Producing Biologically-Adjusted Light filed Dec. 5, 2011, the contents of which are incorporated in their entirety herein by reference except to the extent disclosure therein is inconsistent with disclosure herein.

FIELD OF THE INVENTION

The present invention relates to systems and methods of providing a lighting device to emit light configured to have various biological effects on an observer.

BACKGROUND OF THE INVENTION

This background information is provided to reveal information believed by the applicant to be of possible relevance to the present invention. No admission is necessarily intended, nor should be construed, that any of the preceding information constitutes prior art against the present invention.

Melatonin is a hormone secreted at night by the pineal gland. Melatonin regulates sleep patterns and helps to maintain the body's circadian rhythm. The suppression of melatonin contributes to sleep disorders, disturbs the circadian rhythm, and may also contribute to conditions such as hypertension, heart disease, diabetes, and/or cancer. Blue light, and the blue light component of polychromatic light, have been shown to suppress the secretion of melatonin. Moreover, melatonin suppression has been shown to be wavelength dependent, and peak at wavelengths between about 420 nm and about 480 nm. As such, individuals who suffer from sleep disorders, or circadian rhythm disruptions, continue to aggravate their conditions when using polychromatic light sources that have a blue light (420 nm-480 nm) component.

Curve A of FIG. 1 illustrates the action spectrum for melatonin suppression. As shown by Curve A, a predicted maximum suppression is experienced at wavelengths around about 460 nm. In other words, a light source having a spectral component between about 420 nm and about 480 nm is expected to cause melatonin suppression. FIG. 1 also illustrates the light spectra of conventional light sources. Curve B, for example, shows the light spectrum of an incandescent light source. As evidenced by Curve B, incandescent light sources cause low amounts of melatonin suppression because incandescent light sources lack a predominant blue component. Curve C, illustrating the light spectrum of a fluorescent light source, shows a predominant blue component. As such, fluorescent light sources are predicted to cause more melatonin suppression than incandescent light sources. Curve D, illustrating the light spectrum of a white light-emitting diode (LED) light source, shows a greater amount of blue component light than the fluorescent or incandescent light sources. As such, white LED light sources are predicted to cause more melatonin suppression than fluorescent or incandescent light sources.

As the once ubiquitous incandescent light bulb is replaced by fluorescent light sources (e.g., compact-fluorescent light bulbs) and white LED light sources, more individuals may begin to suffer from sleep disorders, circadian rhythm disorders, and other biological system disruptions. One solution may be to simply filter out all of the blue component (420 nm-480 nm) of a light source. However, such a simplistic approach would create a light source with unacceptable color rendering properties, and would negatively affect a user's photopic response.

SUMMARY OF THE INVENTION

With the foregoing in mind, embodiments of the present invention are related to light sources and, more specifically, to a light-emitting diode (LED) lamp for producing a biologically-adjusted light.

Provided herein are exemplary embodiments of a tuned LED lamp comprising a housing, a drive circuit disposed within the housing and configured to electrically couple to a power source, and a plurality of LED dies mounted on a support coupled to the housing. Each of the plurality of LED dies is electrically coupled to and driven by the drive circuit. The plurality of LED dies may comprise mint, hyper red, and blue LED dies in a ratio of 15 mint LED dies to 5 hyper red LED dies to 4 blue LED dies. Furthermore, the plurality of LED dies may be serially connected.

The drive circuit may be configured to operate the plurality of LED dies such that a relative peak intensity of light emitted by the blue LED dies is within the range from 90% to 100% of a peak intensity of light emitted by the hyper red LED dies and a relative peak intensity of light emitted by the mint LED dies is within the range from 50% to 60% of the peak intensity of light emitted by the hyper red LED dies. Additionally, the drive circuit may be configured to operate the plurality of LED dies to emit light having a color temperature of at least 6,200 K. Furthermore, the drive circuit may be configured to operate the plurality of LED dies to emit light having a color rendering index of at least 90.

Another embodiment according to the present invention may be a tuned LED lamp comprising a housing, a drive circuit disposed within the housing and configured to electrically couple to a power source, and a plurality of LED dies mounted on a support coupled to the housing. Each of the plurality of LED dies is electrically coupled to and driven by the drive circuit. Furthermore, the plurality of LED dies may comprise mint, hyper red, and blue LED dies in a ratio of 1 mint LED die to 1 hyper red LED die to 1 blue LED die.

In some embodiments, the drive circuit may be configured to operate the plurality of LED dies such that a relative peak intensity of light emitted by the blue LED dies is within the range from 80% to 90% of a peak intensity of light emitted by the hyper red LED dies and a relative peak intensity of light emitted by the mint LED is within the range from 30% to 40% of the peak intensity of light emitted by the hyper red LED dies. Furthermore, the plurality of LED dies may comprise 7 mint LED dies, 7 hyper red LED dies, and 7 blue LED dies. Additionally, the plurality of LED dies may comprise the mint LED dies are serially connected, the hyper red LED dies are serially connected, and the blue LED dies are serially connected.

In some embodiments, the drive circuit may be configured to deliver power to the plurality of LED dies in the ratio of 6.9 watts to the mint LED dies to 3.2 watts to the hyper red LED dies to 2.0 watts to the blue LED dies.

Another embodiment according to the present invention may be a tuned LED lamp comprising a housing, a drive circuit disposed within the housing and configured to electrically couple to a power source, and a plurality of LED dies mounted on a support coupled to the housing. Each of the plurality of LED dies is electrically coupled to and driven by the drive circuit. Furthermore, the plurality of LED dies may include at least one blue LED die, at least one hyper red LED die and at least one mint LED die. Additionally, the drive circuit may be configured to operate the plurality of LED dies such that a relative peak intensity of light emitted by the at least one blue LED dies is within the range from 90% to 100% of a peak intensity of light emitted by the at least one hyper red LED dies and a relative peak intensity of light emitted by the at least one mint LED dies is within the range from 50% to 60% of the peak intensity of light emitted by the hyper red LED dies. In some embodiments, the plurality of LED dies comprises a ratio of 15 mint LED dies to 5 hyper red LED dies to 4 blue LED dies. Furthermore, the plurality of LED dies may be serially connected.

Various aspects and alternative embodiments are described below.

BRIEF DESCRIPTION OF THE DRAWINGS

FIGS. 10A and 10B present color bin data for a mint LED die used III one embodiment presented herein.

DETAILED DESCRIPTION OF THE PREFERRED EMBODIMENT

Melatonin is a hormone secreted at night by the pineal gland. Melatonin regulates sleep patterns and helps to maintain the body's circadian rhythm. The suppression of melatonin contributes to sleep disorders, disturbs the circadian rhythm, and may also contribute to conditions such as hypertension, heart disease, diabetes, and/or cancer. Blue light, and the blue light component of polychromatic light, have been shown to suppress the secretion of melatonin. Moreover, melatonin suppression has been shown to be wavelength dependent, and peak at wavelengths between about 420 nm and about 480 nm. As such, individuals who suffer from sleep disorders, or circadian rhythm disruptions, continue to aggravate their conditions when using polychromatic light sources that have a blue light (420 nm-480 nm) component.

Figure 1:
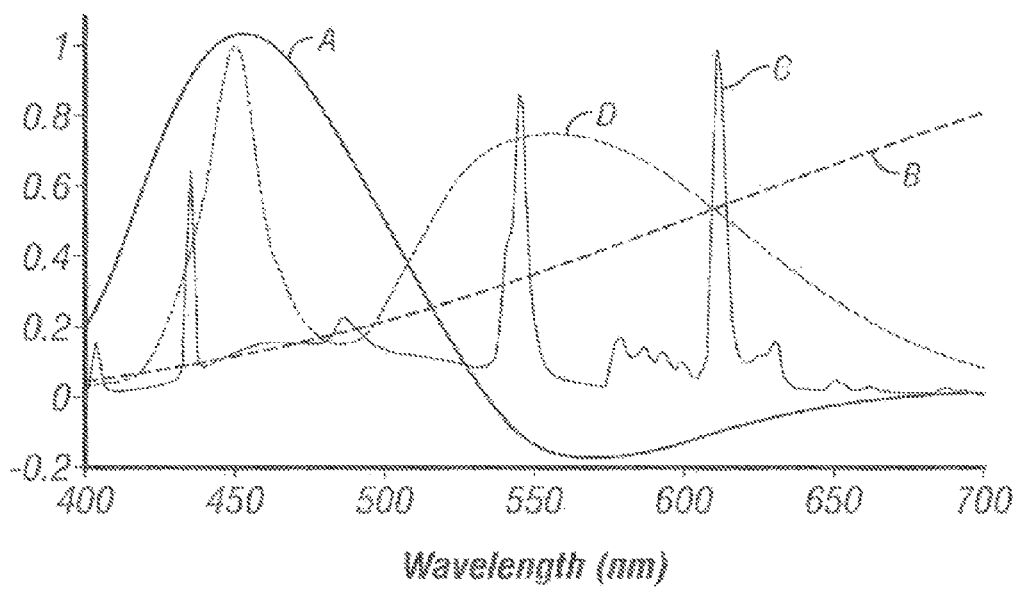
FIG. 1 illustrates the light spectra of conventional light sources in comparison to a predicted melatonin suppression action spectrum for polychromatic light.

Curve A of FIG. I illustrates the action spectrum for melatonin suppression. As shown by Curve A, a predicted maximum suppression is experienced at wavelengths around about 460 nm. In other words, a light source having a spectral component between about 420 nm and about 480 nm is expected to cause melatonin suppression. FIG. 1 also illustrates the light spectra of conventional light sources. Curve B, for example, shows the light spectrum of an incandescent light source. As evidenced by Curve B, incandescent light sources cause low amounts of melatonin suppression because incandescent light sources lack a predominant blue component. Curve C, illustrating the light spectrum of a fluorescent light source, shows a predominant blue component. As such, fluorescent light sources are predicted to cause more melatonin suppression than incandescent light sources. Curve D, illustrating the light spectrum of a white light-emitting diode (LED) light source, shows a greater amount of blue component light than the fluorescent or incandescent light sources. As such, white LED light sources are predicted to cause more melatonin suppression than fluorescent or incandescent light sources.

As the once ubiquitous incandescent light bulb is replaced by fluorescent light sources (e.g., compact-fluorescent light bulbs) and white LED light sources, more individuals may begin to suffer from sleep disorders, circadian rhythm disorders, and other biological system disruptions. One solution may be to simply filter out all of the blue component (420 nm-480 nm) of a light source. However, such a simplistic approach would create a light source with unacceptable color rendering properties, and would negatively affect a user's photopic response.

On the other hand, because exposure to light generally, and blue light in particular, can reduce the level of drowsiness by suppressing the secretion of melatonin, exposure to light can be employed to maintain alertness when needed. Additionally, exposure to enhanced the blue light intensities can help to reset, or shift, the phase of the circadian rhythm of an individual. As such, phase-shifting can be useful in a variety of situations when resetting an individual's internal body clock is desired. Examples include: avoiding jetlagged after inter-continental travel, or maintaining alertness for shift-workers who are engaged in nighttime work. Although varying the intensity of the blue spectral component of a light source can be achieved through simple filtering, such filtering results in a non-optimal lighting environment.

As such, presenting herein is an LED lamp with commercially acceptable color rendering properties, which can be tuned to produce varying light outputs. In one embodiment, the light output produces minimal melatonin suppression, and thus has a minimal effect on natural sleep patterns and other biological systems. The LED lamp may also be tuned to generate different levels of blue light, appropriate for the given circumstance, while maintaining good light quality and a high CRI in each case. The LED lamp may also be configured to "self-tune" itself to generate the appropriate light output spectrum, depending on factors such as the lamp's location, use, ambient environment, etc.

The light output states/configurations achievable by the LED lamps presented include: a pre-sleep configuration, a phase-shift configuration, and a general lighting configuration. In the pre-sleep configuration, the lamp generates a reduced level of blue light in order to provide an adequate working environment while significantly lessening the suppression of melatonin. The spectrum of light produced by the lamp in the pre-sleep configuration provides an environment appropriate for preparing for sleep while still maintaining light quality. In the phase-shifting configuration, the lamp generates an increased level of blue light, thereby greatly diminishing melatonin production. The spectrum of light produced by the lamp in this phase-shifting configuration provides an environment for shifting the phase of an individual's circadian rhythm or internal body clock. In the general lighting configuration, the lamp generates a normal level blue light, consistent with a typical light spectrum (e.g., daylight). In all states, however, the lamp maintains high visual qualities and CRI, in order to provide an adequate working environment.

In one embodiment, the ability to tune, or adjust, the light output is provided by employing a specific combination of LED dies of different colors, and driving the LED dies at various currents to achieve the desired light output. In one embodiment, the LED lamp employs a combination of red, blue, cyan, and mint LED dies, such that the combination of dies produces a desired light output, while maintaining high quality light and high CRI.

The following detailed description of the figures refers to the accompanying drawings that illustrate an exemplary embodiment of a tunable LED lamp for producing a biologically-adjusted light output. Other embodiments are possible. Modifications may be made to the embodiment described herein without departing from the spirit and scope of the present invention. Therefore, the following detailed description is not meant to be limiting.

Figure 2:
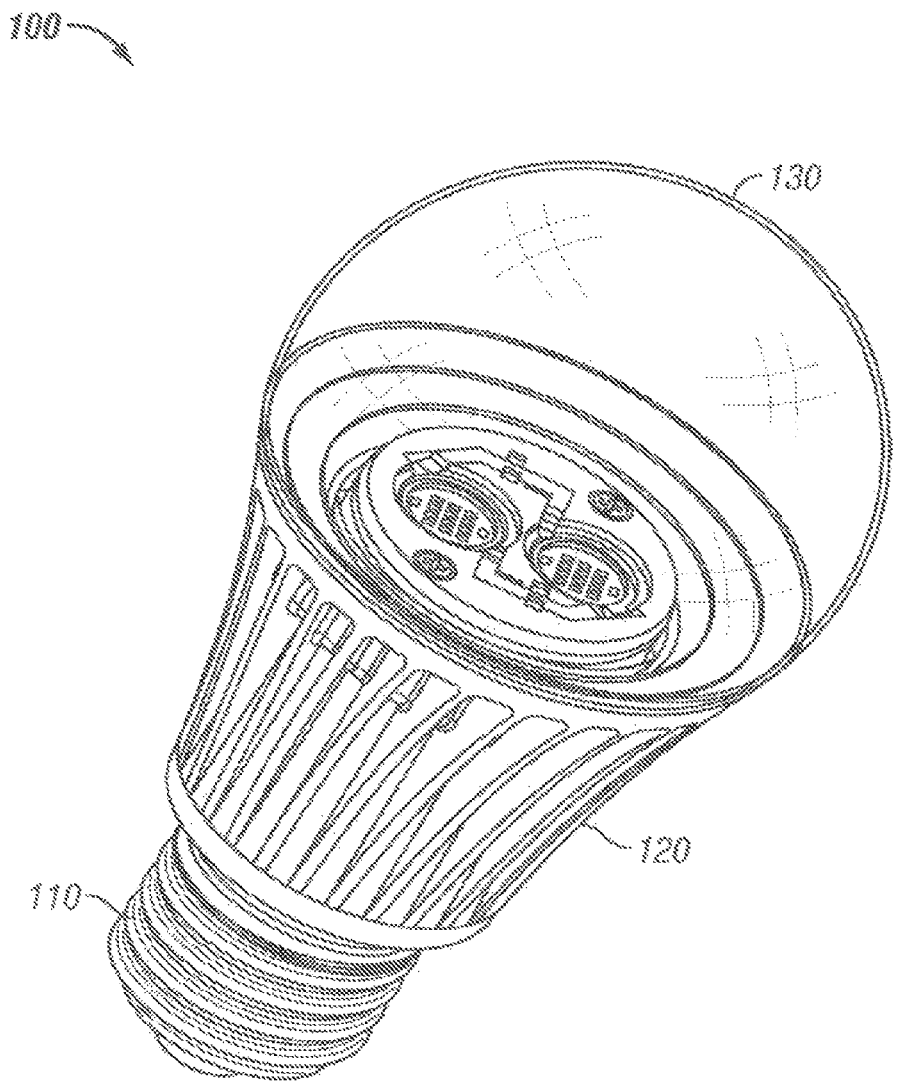
FIG. 2 is a perspective view of an LED lamp in accordance with one embodiment presented herein.

FIG. 2 is a perspective view of an LED lamp (or bulb) 100 in accordance with one embodiment presented herein. In general, LED lamp 100 is appropriately designed to produce biologically-adjusted light, while still maintaining a commercially acceptable color temperature and commercially acceptable color rending properties.

The term "biologically-adjusted light" is intended to mean "a light that has been modified to manage biological effects on a user." The term "biological effects" is intended to mean "any impact or change a light source has to a naturally occurring function or process." Biological effects, for example, may include hormone secretion or suppression (e.g., melatonin suppression), changes to cellular function, stimulation or disruption of natural processes, cellular mutations or manipulations, etc.

As shown in FIG. 2, LED lamp 100 includes a base 110, a heat sink 120, and an optic 130. As will be described below, LED lamp 100 further includes one or more LED chips and dedicated circuitry Base 110 is preferably an Edison-type screw-m shell. Base 110 is preferably formed of an electrically conductive material such as aluminum. In alternative embodiments, base 110 may be formed of other electrically conductive materials such as silver, copper, gold, conductive alloys, etc. Internal electrical leads (not shown) are attached to base 110 to serve as contacts for a standard light socket (not shown). Additionally, base 110 may be adapted to be any type of lamp base known in the art, including, but not limited to, bayonet, bi-post, bi-pin and wedge bases.

As known in the art, the durability of an LED chip is usually affected by temperature. As such, heat sink 120, and structures equivalent thereto, serves as means for dissipating heat away from one or more of the LED chips within LED lamp 100. In FIG. 2, heat sink 120 includes fins to increase the surface area of the heat sink. Alternatively, heat sink 120 may be formed of any configuration, size, or shape, with the general intention of drawings heat away from the LED chips within LED lamp 100. Heat sink 120 is preferably formed of a thermally conductive material such as aluminum, copper, steel, etc.

Optic 130 is provided to surround the LED chips within LED lamp 100. As used herein, the terms "surround" or "surrounding" are intended to mean partially or fully encapsulating. In other words, optic 130 surrounds the LED chips by partially or fully covering one or more LED chips such that light produced by one or more LED chips is transmitted through optic 130. In the embodiment shown, optic 130 takes a globular shape. Optic 130, however, may be formed of alternative forms, shapes, or sizes. In one embodiment, optic 130 serves as an optic diffusing element by incorporating diffusing technology, such as described in U.S. Pat. No. 7,319,293 (which is incorporated herein by reference in its entirety). In such an embodiment, optic 130, and structures equivalent thereto, serves as a means for defusing light from the LED chips. In alternative embodiments, optic 130 may be formed of a light diffusive plastic, may include a light diffusive coating, or may having diffusive particles attached or embedded therein.

In one embodiment, optic 130 includes a color filter applied thereto. The color filter may be on the interior or exterior surface of optic 130. The color filter is used to modify the light output from one or more of the LED chips. In one embodiment, the color filter is a ROSCOLUX #4530 CAL-COLOR 30 YELLOW. In alternative embodiments, the color filter may be configured to have a total transmission of about 75%, a thickness of about 50 microns, and/or may be formed of a deep-dyed polyester film on a polyethylene terephthalate (PET) substrate.

In yet another embodiment, the color filter may be configured to have transmission percentages within +/−10%, at one or more wavelengths, in accordance with the following table:

| Wavelength | Transmission (%) |
|---|---|
| 360 380 400 420 440 | 66 64 49 30 22 |

Figure 3:
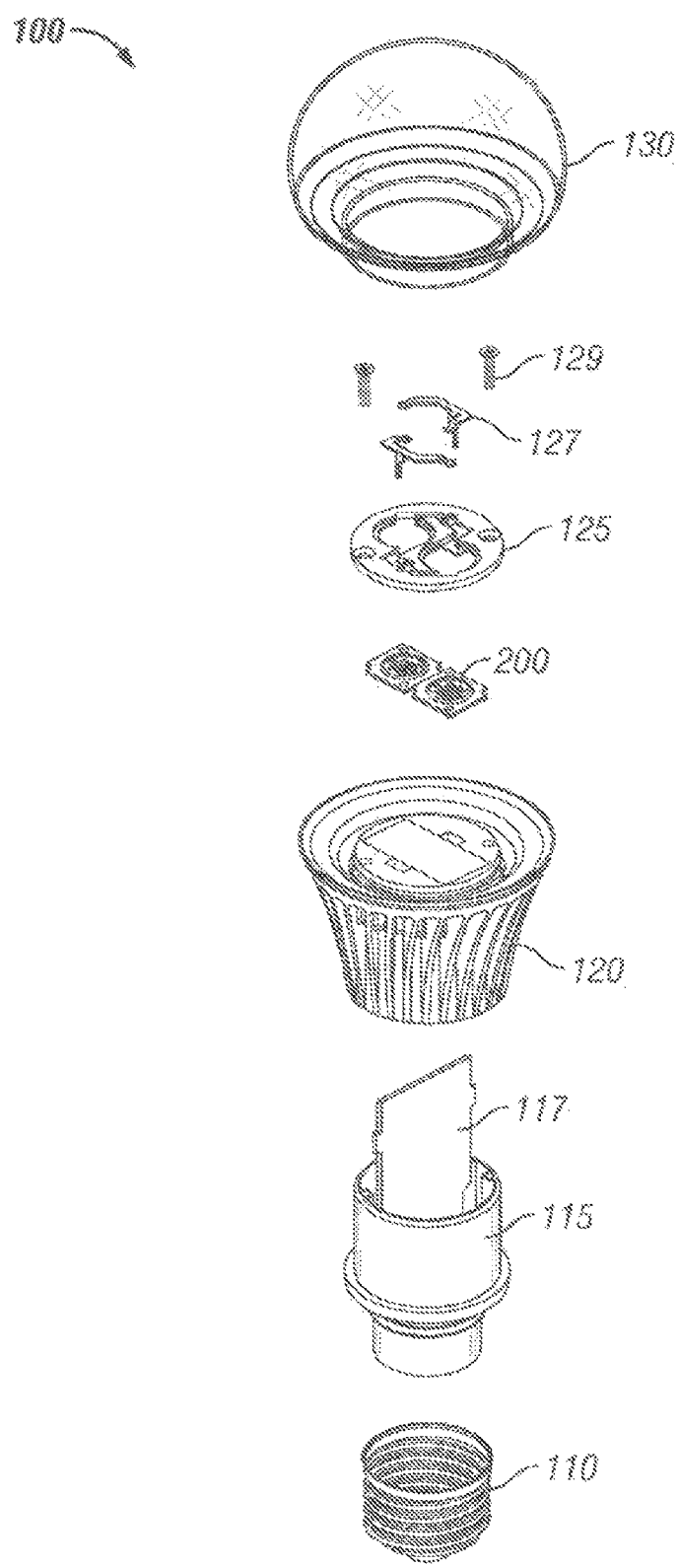
FIG. 3 is an exploded view of the LED lamp of FIG. 2.

FIG. 3 is an exploded view of LED lamp 100, illustrating internal components of the lamp. FIGS. 4-7 are exploded views of portions of LED lamp 100. FIGS. 3-7 also serve to illustrate how to assemble LED lamp 100. As shown, in addition to the components described above, LED lamp 100 also includes at least a housing 115, a printed circuit board (PCB) 117, one or more LED chips 200, a holder 125, spring wire connectors 127, and screws 129.

As described in more detail with reference to FIG. 8, PCB 117 includes dedicated circuitry, such as power supply 450, driver circuit 440, and output-select controller 445. The circuitry on PCB 117 and equivalents thereof serves as a means for driving the LED chips 200 (or individual LED dies) to produce a biologically-adjusted light output.

Figure 9:
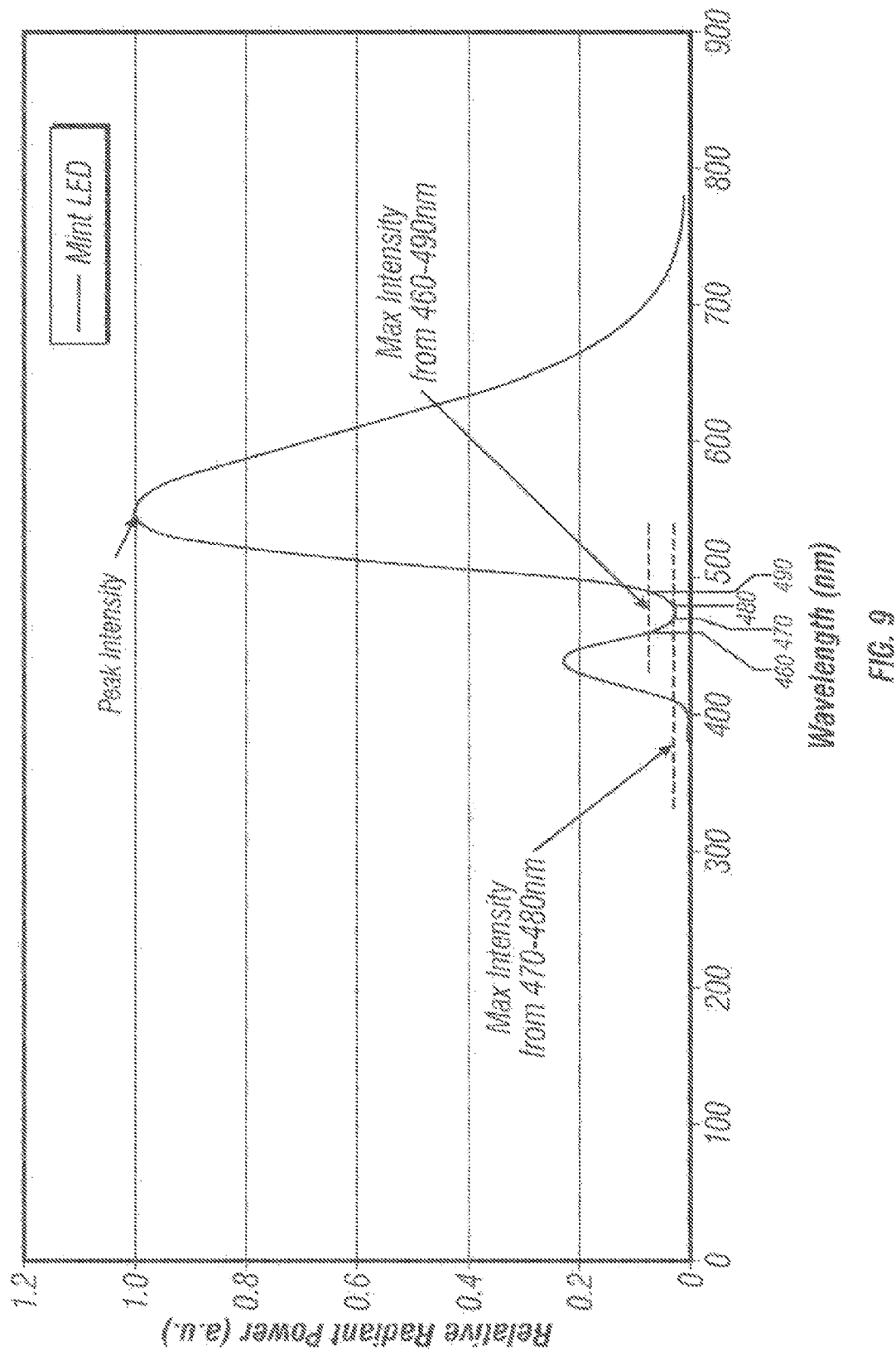
FIG. 9 illustrates a relative radiant power curve for a mint LED die used in one embodiment presented herein.
Figure 10A:
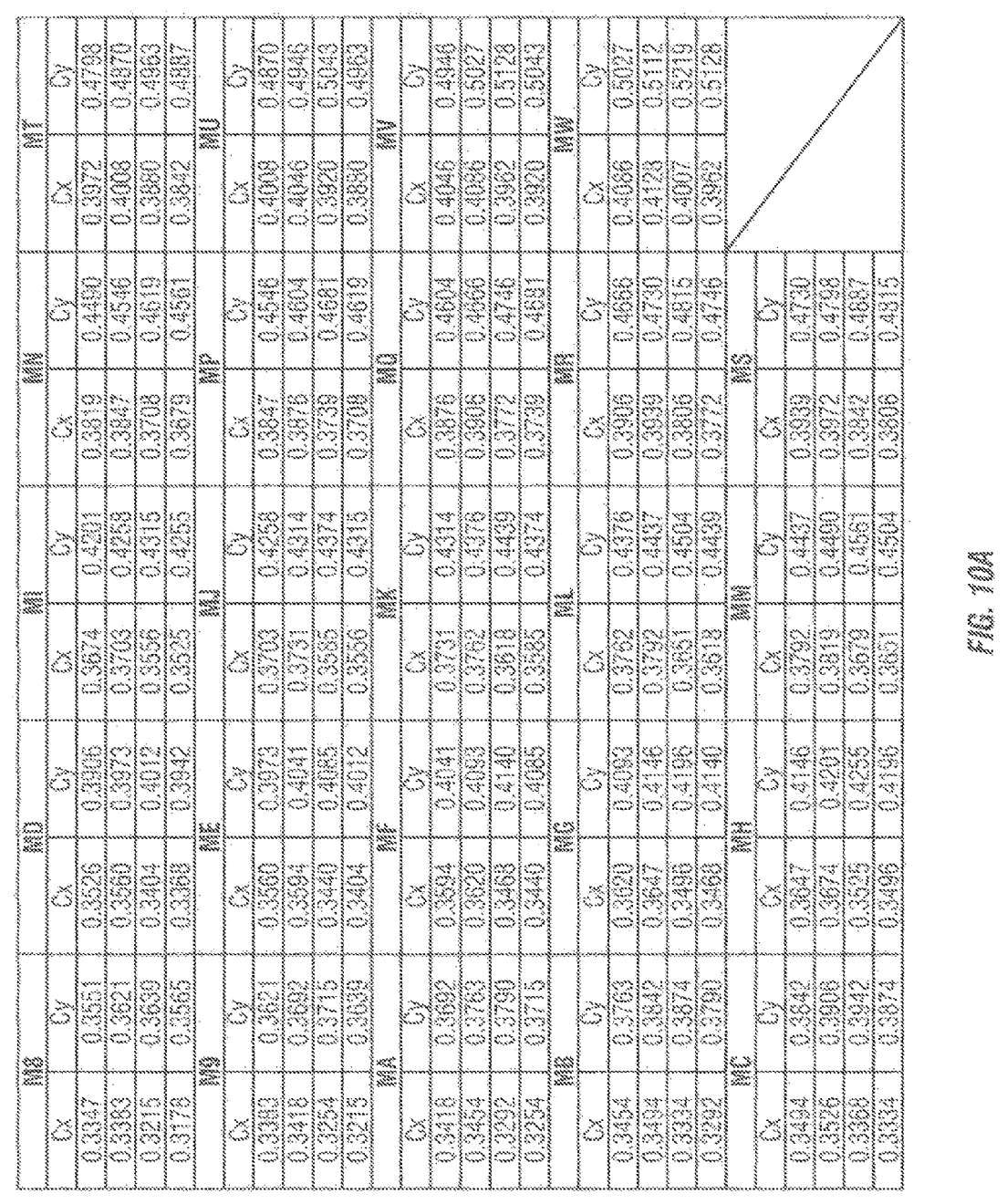
Figure 10B:
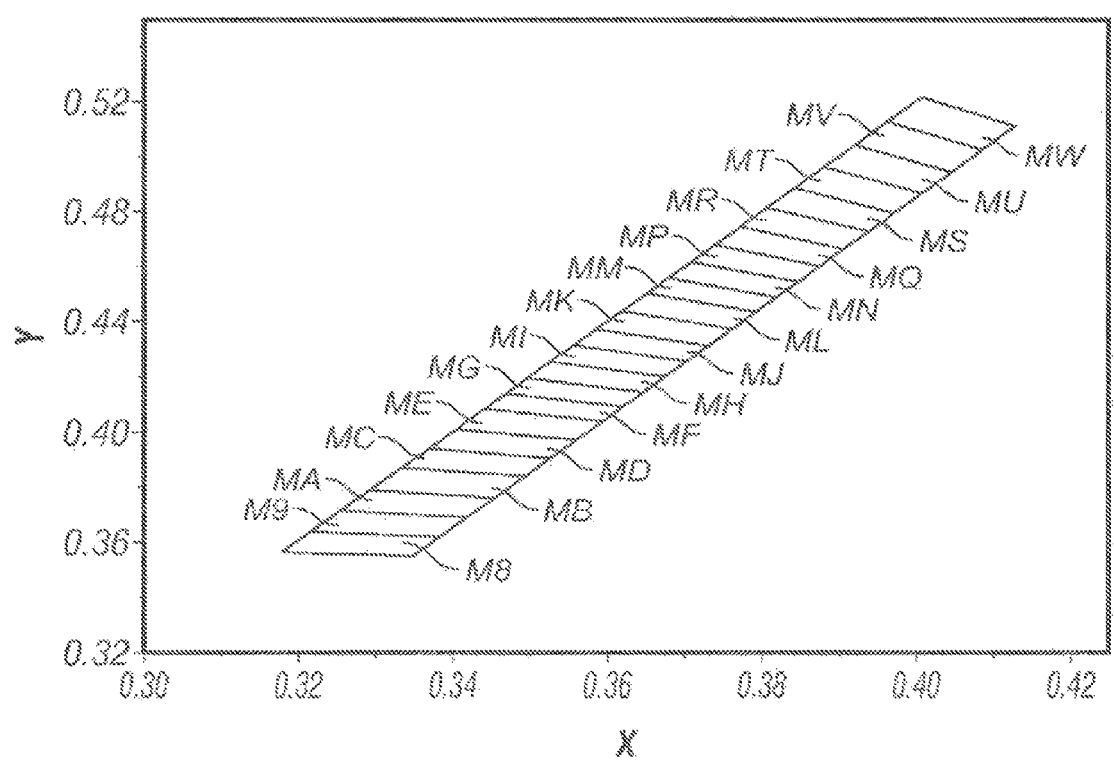
Figure 11:
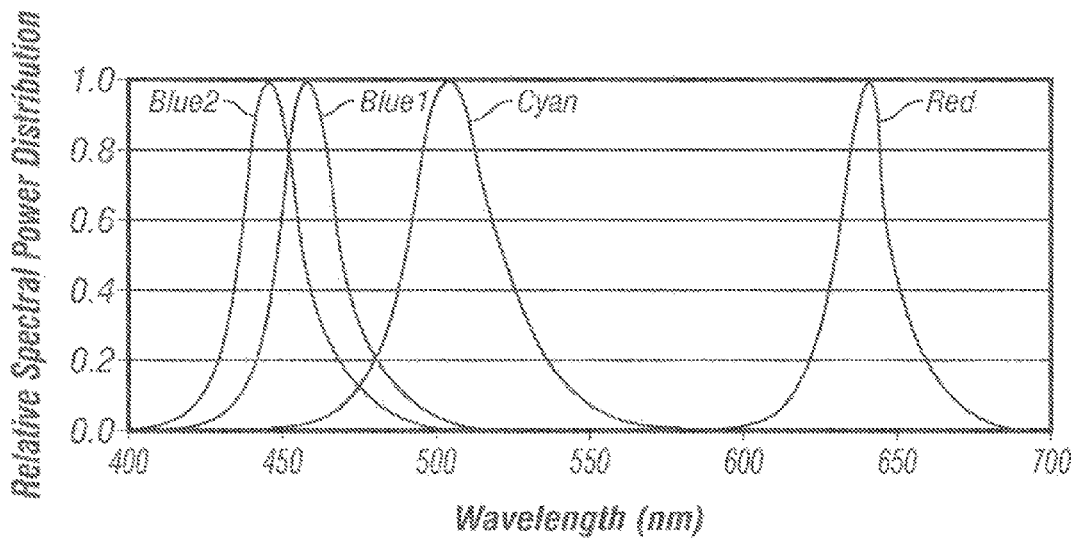
FIG. 11 shows relative spectral power distributions for red, cyan, and blue LED dies that are used in one embodiment presented.

As used herein, the term "LED chip(s)" is meant to broadly include LED die(s), with or without packaging and reflectors, that may or may not be treated (e.g., with applied phosphors). In the embodiment shown, however, each LED chip 200 includes a plurality of LED dies. In one embodiment, LED chips 200 include an LED package comprising a plurality of LED dies, with at least two different colors, driven at varying currents to produce the desired light output and spectral power densities. Preferably, each LED chip 200 includes two red LED dies, three cyan LED dies, four mint LED dies, and three blue LED dies. FIG. 9 illustrates a relative radiant power curve for a mint LED die used in one embodiment presented herein. FIGS. 10A and 10B present color bin data for a mint LED die used in one embodiment presented herein. FIG. 11 shows relative spectral power distributions for red (or alternatively red-orange), cyan, and (two alternative) blue LED dies that are used in one embodiment presented (with alternative equivalent LED dies also being within the scope of the present invention). With this unique combinations of dies, together with the means for driving the LED chips, each of the above mentioned bio-effective states/configurations (e.g., pre-sleep, phase-shifting, and/or general lighting) can be obtained with good color rendering properties.

In one embodiment the tunable LED lamp operates in the pre-sleep configuration such that the radiant power emitted by the dies is in a ratio of: about 1 watt of radiant power generated by the mint LED dies, to about 0.5 watts of radiant power generated by the red-orange LED dies, to about 0.1 watts of radiant power generated by the cyan LED dies. In this embodiment the tunable LED lamp operates in the general lighting configuration such that the radiant power emitted by the dies is in a ratio about 1 watt of radiant power generated by the mint LED dies, to about 0.3 watts of radiant power generated by the red-orange LED dies, to about 0.4 watts of radiant power generated by the cyan LED dies, to about 0.2 watts of radiant power generated by the blue LED dies. In this embodiment, the tunable LED lamp operates in the phase-shift configuration such that the radiant power emitted by the dies is in a ratio of about 1 watt of radiant power generated by the mint LED dies, to about 0.1 watts of radiant power generated by the red-orange LED dies, to about 0.2 watts of radiant power generated by the cyan LED dies, to about 0.4 watts of radiant power generated by the blue LED dies.

In another embodiment, the tunable LED lamp operates in the pre-sleep configuration such that the radiant power emitted by the dies is in a ratio of: about 1 watt of radiant power generated by the mint LED dies, to about 0.8 watts of radiant power generated by the red-orange LED dies, to about 0.3 watts of radiant power generated by the cyan LED dies. In this embodiment, the tunable LED lamp operates in the general lighting configuration such that the radiant power emitted by the dies is in a ratio about 1 watt of radiant power generated by the mint LED dies, to about 0.2 watts of radiant power generated by the red-orange LED dies, to about 0.2 watts of radiant power generated by the blue LED dies. In this embodiment, the tunable LED lamp operates in the phase-shift configuration such that the radiant power emitted by the dies is in a ratio of about 1 watt of radiant power generated by the mint LED dies, to about 0.1 watts of watts of radiant power generated by the red-orange LED dies, to about 0.5 watts of radiant power generated by the blue LED dies.

For example, to achieve a pre-sleep configuration, driver circuit 440 may be configured to drive the plurality of LED dies such that a blue output intensity level, in a visible spectral output range of between about 380 nm and about 485 nm, is less than about 10% of a relative spectral power of any other peaks in the visible spectral output above about 485 nm. In one embodiment, driver circuit 440 drives the plurality of LED dies such that about 150 mA of current is delivered to four mint LED dies; about 360 mA of current is delivered to two red LED dies; and about 40 mA of current is delivered to three cyan LED dies. In another embodiment, wherein a color filter as described above is employed, the pre-sleep configuration is achieved by configuring driver circuit 440 to deliver about 510 MA of current to 4 mint LED dies.

To achieve a phase-shift configuration, driver circuit 440 may be configured to drive the plurality of LED dies such that a blue output intensity level, in a visible spectral output range of between about 455 nm and about 485 nm, is greater than about 125% (or greater than about 150%; or greater than about 200%) of a relative spectral power of any other peaks in the visible spectral output above about 485 nm. The color rendering index in the phase-shift configuration may be greater than 80. In one embodiment, driver circuit 440 drives the plurality of LED dies such that about 510 mA of current is delivered to the mint LED dies; about 180 mA of current is delivered to the red LED dies; about 40 mA of current is delivered to the cyan LED dies; and about 100 mA of current is delivered to the blue LED dies.

To achieve a general lighting configuration, driver circuit 440 may be configured to drive the plurality of LED dies such that a blue output intensity level, in a visible spectral output range of between about 380 nm and about 485 nm, is between about 100% to about 20% of a relative spectral power of any other peaks in the visible spectral output above about 485 nm. The color rendering index in the general lighting configuration may be greater than 85. In one embodiment, driver circuit 440 drives the plurality of LED dies such that about 450 mA of current is delivered to the mint LED dies; about 230 mA of current is delivered to the red LED dies; about 110 mA of current is delivered to the cyan LED dies; and about 60 mA of current is delivered to the blue LED dies.

Figure 4:
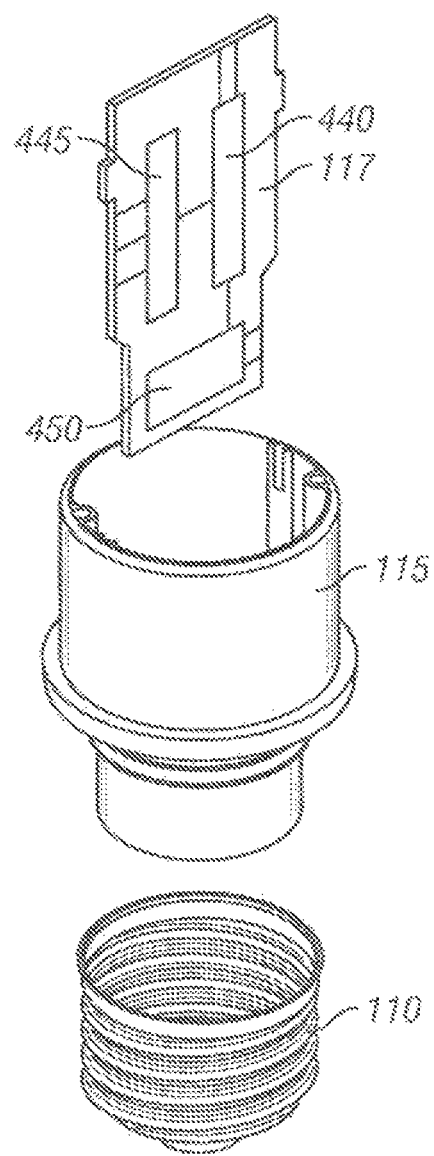
FIG. 4 is an exploded view of a portion of the LED lamp of FIG. 2.

In one embodiment, driver circuit 440 is configured to drive LED chips 200 with a ripple current at frequencies greater than 200 Hz. A ripple current at frequencies above 200 Hz is chosen to avoid biological effects that may be caused by ripple currents at frequencies below 200 Hz. For example, studies have shown that some individuals are sensitive to light flicker below 200 Hz, and in some instances experience aggravated headaches, seizures, etc As shown in FIG. 4, base 110 is glued or crimped onto housing 115. PCB 117 is mounted within housing 115. Insulation and/or potting compound (not shown) may be used to secure PCB 117 within housing 115. Electrical leads on PCB 117 are coupled to base 110 to form the electrical input leads of LED lamp 100.

In some embodiments, base 110 may be adapted to facilitate the operation of the LED lamp based upon receiving an electrical signal from a light socket that base 110 may be attached to. For example, base 110 may be adapted to receive electrical signals from the socket of a three-way lamp, as is known in the art. Furthermore, driver circuit 440 may similarly be adapted to receive electrical signals from base 110 in such a fashion so as to use the electrical signals from the three-way lamp as an indication of which emitting configuration is to be emitted. The modes of operation of a three-way lamp are known in the art. Base 110 and driver circuit 440 may be adapted to cause the emission of the phase-shift configuration upon receiving a first electrical signal from the socket of a three-way lamp, the general illumination configuration upon receiving a second electrical signal from the three-way lamp, and the pre-sleep configuration upon receiving a third electrical signal from the three-way lamp.

More specifically, as is known in the art, base 110 may include a first terminal (not shown) and a second terminal (not shown), the first terminal being configured to electrically couple to a low-wattage contact of a three-way fixture, and the second terminal being configured to electrically couple to a medium-wattage contact of a three-way fixture. Driver circuit 440 may be positioned in electrical communication with each of the first and second terminals of base 110. When base 110 receives an electric signal at the first terminal, but not at the second terminal, the driver circuit 440 may detect such and may cause the emission of light according to one of the phase-shift configuration, the general illumination configuration, and the pre-sleep configuration. When base 110 receives an electrical signal at the second terminal, but not at the first terminal, the driver circuit 440 may detect such and may cause the emission of light according to one of the phase-shift configuration, the general illumination configuration, and the pre-sleep configuration, but not the same configuration as when an electrical signal was detected at the first terminal and not the second. Finally, base 110 receives an electrical signal at both the first terminal and the second terminal, driver circuit 440 may detect such and may cause the emission of light according to one of the phase-shift configuration, the general illumination configuration, and the pre-sleep configuration, but not the same configuration as is emitted when an electrical signal is detected at only one of the first or second terminals of base 110.

Furthermore, in some embodiments, the driver circuit 440 may be configured to cause the emission of light according to any of the configurations as described hereinabove based upon the waveform of an electrical signal received by base 110 and detected by driver circuit 440. For example, in some embodiments, driver circuit 440 may be configured to cause the emission of light that is responsive to a TRIAC signal. A TRIAC signal is a method of manipulating the waveform of an AC signal that selectively "chops" the waveform such that only certain periods of the waveform within an angular range are transmitted to an electrical device, and is used in lighting.

Driver circuit 440 may be configured to cause the emission of light according to one of the various configurations of light responsive to varying ranges of TRIAC signals. A range of a TRIAC signal may be considered as a portion of a continuous, unaltered AC signal. A first TRIAG signal range may be a range from greater than about 0% to about 33% of an AC signal. This range may correspond to a percentage of the total angular measurement of a single cycle of the AC signal. Accordingly, where the single cycle of the AC signal is approximately $2\pi$ radians, the first range may be from greater than about 0 to about $0.67\pi$ radians. It is contemplated that angular measurement of the TRIAC signal is only one method of defining a range of a characteristic of the TRIAC signal. Other characteristics include, but are not limited to, phase angle, voltage, RMS voltage, and any other characteristic of an electric signal. Accordingly, the driver circuit 440 may include circuitry necessary to determine any of the phase angle, voltage, and RMS voltage of a received signal. The driver circuit 440 may be configured to detect the TRIAC signal and determine it falls within this range, and may further be configured to cause the emission of light according to one of the phase-shift configuration, the general illumination configuration, and the pre-sleep configuration. A second TRIAC signal range may be from about 33% to about 67% of an AC signal, which may correspond to a range from about $0.67\pi$ to about $1.33\pi$ radians. The driver circuit 440 may be configured to detect the TRIAC signal and determine it falls within this range, and may further be configured to cause the emission of light according to one of the phase-shift configuration, the general illumination configuration, and the pre-sleep configuration, but not the configuration that was emitted when the driver circuit determined the TRIAC signal was within the first TRIAC signal range. A third TRIAC signal range may be from about 67% to about 100% of an AC signal, which may correspond to a range from about $1.33\pi$ to about $2\pi$ radians. The driver circuit 440 may be configured to detect the TRIAC signal and determine it falls within this range, and may further be configured to cause the emission of light according to one of the phase-shift configuration, the general illumination configuration, and the pre-sleep configuration, but not the configuration that was emitted when the driver circuit determined the TRIAC signal was within either of the first TRIAC signal range or the second TRIAC signal range.

In another embodiment, a first TRIAC signal range may be from about 0% to about 25% of an AC signal, corresponding to within a range from about 0 to about $0.5\pi$ radians. Driver circuit 440 may be configured to detect the TRIAC signal and determine if it falls within this range, and may further be configured to not emit light. A second TRIAC signal range may be from about 25% to about 50% of an AC signal, corresponding to within a range from about $0.5\pi$ to about $1.0\pi$ radians. Driver circuit 440 may be configured to detect the TRIAC signal and determine if it falls within this range, and may further be configured to cause the emission of light according to one of the phase-shift configuration, the general illumination configuration, and the pre-sleep configuration. A third TRIAC signal range may be from about 50% to about 75% of an AC signal, corresponding to within a range from about $1.0\pi$ to about $1.5\pi$ radians. Driver circuit 440 may be configured to detect the TRIAC signal and determine if it falls within this range, and may further be configured to cause the emission of light according to one of the phase-shift configuration, the general illumination configuration, and the pre-sleep configuration, but not the configuration that was emitted when the driver circuit determined the TRIAC signal was within the second TRIAC signal range. A fourth TRIAC signal range may be from about 75% to about 100% of an AC signal, corresponding to a range from about $1.5\pi$ to about 2.0 radians. Driver circuit 440 may be configured to detect the TRIAC signal and determine if it falls within this range, and may further be configured to cause the emission of light according to one of the phase-shift configuration, the general illumination configuration, and the pre-sleep configuration, but not the configuration that was emitted when the driver circuit determined the TRIAC signal was within either of the second or third TRIAC signal ranges.

In order to enable the operation of an LED lamp 100 that is responsive to an electrical signal, such as a wireless signal or a TRIAC signal, it may be necessary to configure the power source for the LED lamp 100 to provide an electrical signal so as to control the operation of the LED lamp 100. Accordingly, in some embodiments, where the LED lamp 100 is electrically coupled to a lighting fixture that is controlled by a wall switch, or where the LED lamp 100 is directly electrically connected to a wall switch, the invention may further comprise a retrofit wall-mounted switch (not shown). In such embodiments, the retrofit wall-mounted switch may operate substantially as the output selection device and the user input device described herein. The retrofit wall-mounted switch may be configured to replace a standard wall switch for control of a light fixture, as is known in the art. The retrofit wall-mounted switch may be configured to generate or manipulate a signal so as to control the operation of the LED lamp 100. For example, in some embodiments, the retrofit wall-mounted switch may be configured to generate a wireless signal that may be received by the LED lamp 100 that may result in the operation of the LED lamp 100 as described hereinabove. Also, in some embodiments, the retrofit wall-mounted switch may be configured to manipulate a power source to which the retrofit wall-mounted switch is electrically coupled so as to generate a TRIAC signal, to which the LED lamp 100 may operate responsively to as described hereinabove. In such embodiments, the retrofit wall-mounted switch may be positioned electrically intermediate the power source and the LED lamp 100.

In some embodiments, base 110 may be configured to be a removably attachable member of LED lamp 100, defined as an intermediate base. In some other embodiments, an intermediate base may be included in addition the base 110. Intermediate base 110 may include structural elements and features facilitating the attachment of intermediate base 110 to a part of LED lamp 100. For example, intermediate base 110 may be adapted to cooperate with a feature or structure of housing 115 so as to removably attach intermediate base 110 thereto. For example, where intermediate base 110 is an Edison-type base having threading adapted to conform to standard threading for such bases, housing 115 may include a threaded section (not shown) configured to engage with the threads of intermediate base 110 so as to removable attach with intermediate base 110. Furthermore, each of intermediate base 110 and LED lamp 100 may include electrical contacts so as to electrically couple LED lamp 100 to intermediate base 110 when intermediate base 110 is attached. The size, position, and configuration of such electrical contacts may vary according to the method of attachment between LED lamp 100 and intermediate base 110.

Additionally, intermediate base 110 may include elements facilitating the transitioning of LED chips 200 between the various configurations, i.e. pre-sleep, phase shift, and general illuminating configurations. For example, in some embodiments, intermediate base 110 may include a user input device (not shown) adapted to receive an input from a user. The input from the user may cause intermediate base 110 to interact with at least one of driver circuit 440 and a power circuit of the LED lamp 100 so as to cause the LED chips 200 to emit light according to any of the configurations recited herein.

In some embodiments, the user input may cause the LED lamp 100 to transition from the present emitting configuration to a selected emitting configuration, or to cease emitting light. In some embodiments, the user input may cause the LED lamp 100 to progress from one emitting configuration to another emitting configuration according to a defined progression. An example of such a progression may be, from an initial state of not emitting light, to emitting the phase-shift configuration, to emitting the general illumination configuration, to emitting the pre-sleep configuration, to ceasing illumination. Such a progression is exemplary only, and any combination and permutation of the various emitting configurations are contemplated and included within the scope of the invention. The base 110 may include circuitry necessary to receive the input from the user and to communicate electrically with the various elements of the LED lamp 100 to achieve such function.

In some embodiments, the user input device may be a device that is physically accessible by a user when the base 110 is attached to the LED lamp 100 and when the LED lamp 100 is installed in a lighting fixture. For example, the user input device may be a lamp turn knob operatively connected to circuitry comprised by the base 110 to affect the transitioning described hereinabove. A lamp turn knob is an exemplary embodiment only, and any other structure or device capable of receiving an input from a user based on electrical and/or mechanical manipulation or operation by the user is contemplated and included within the scope of the invention. In some embodiments, the user input device may be an electronic communication device including a wireless communication device configured to receive a wireless signal from the user as the input. Such user input devices may be adapted to receive a user input in the form of an infrared signal, a visible light communication (VLC) signal, radio signal, such as Wi-Fi, Bluetooth, Zigbee, cellular data signals, Near Field Communication (NFC) signal, and any other wireless communication standard or method known in the art. Additionally, in some embodiments, the user input device may be adapted to receive an electronic signal from the user via a wired connection, including, but not limited to, Ethernet, universal serial bus (USB), and the like. Furthermore, where the user input device is adapted to establish an Ethernet connection, the user input device may be adapted to receive power from the Ethernet connection, conforming to Power-over-Ethernet (PoE) standards. In such embodiments, the power received by the user input device may provide power to the LED lamp 100 enabling its operation.

In some embodiments, it is contemplated that any of the lighting devices as described herein may be integrally formed with a lighting fixture, where the LED lamp 100 is not removably attachable to the lighting fixture. More specifically, in some embodiments, those aspects of the lighting devices described herein that are included to permit the attachability of the lighting device to a separately-produced lighting fixture may be excluded, and those aspects directed to the function of emitting light according to the various lighting configurations as described herein may be included. For example, in the present embodiment, the base 110 may be excluded, and the driver circuit 440 may be directly electrically coupled to an external power source or to an electrical conduit thereto. Furthermore, the geometric configuration of optic 130, heat sink 120, LED chips 200, and all other elements of the LED lamp 100 may be adapted to facilitate a desired configuration of an integrally-formed lighting fixture.

Figure 5:
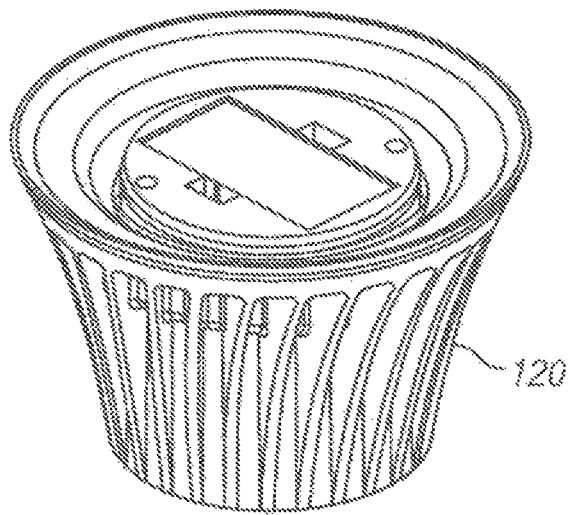
FIG. 5 is an exploded view of a portion of the LED lamp of FIG. 2.
Figure 5:
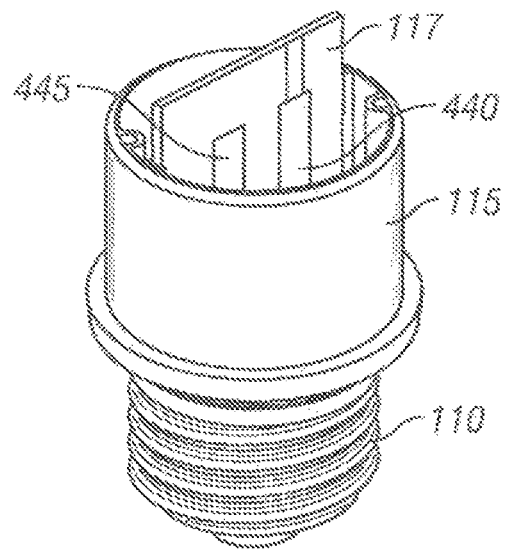
Figure 6:
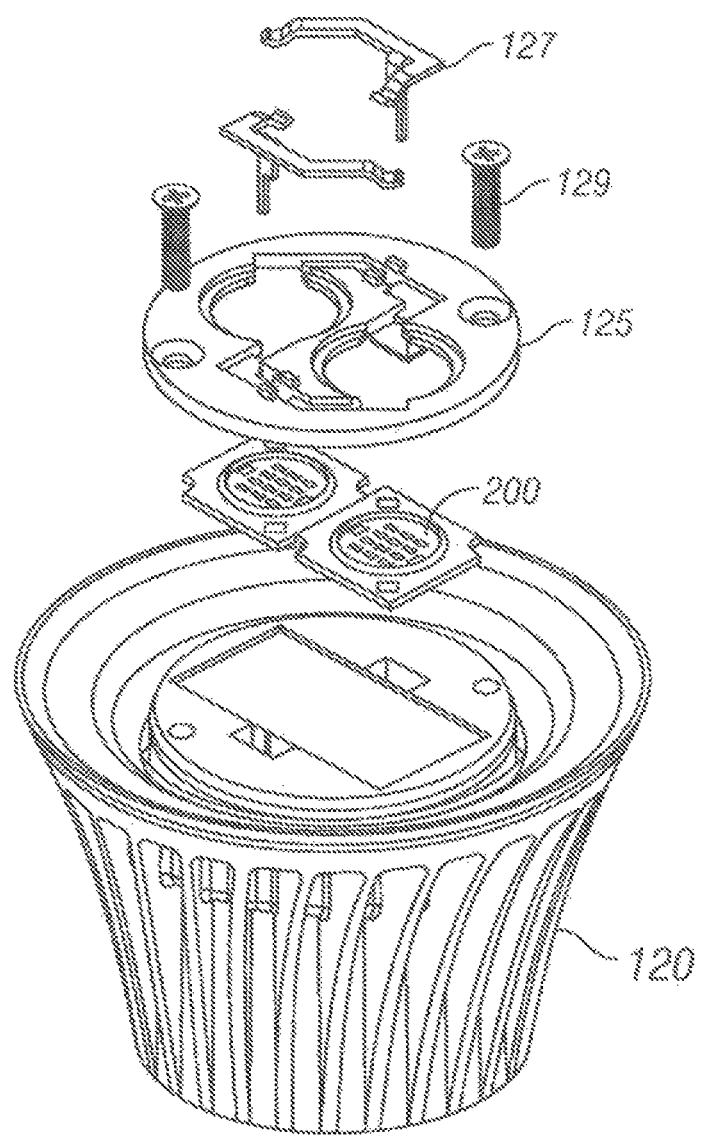
FIG. 6 is an exploded view of a portion of the LED lamp of FIG. 2.
Figure 7:
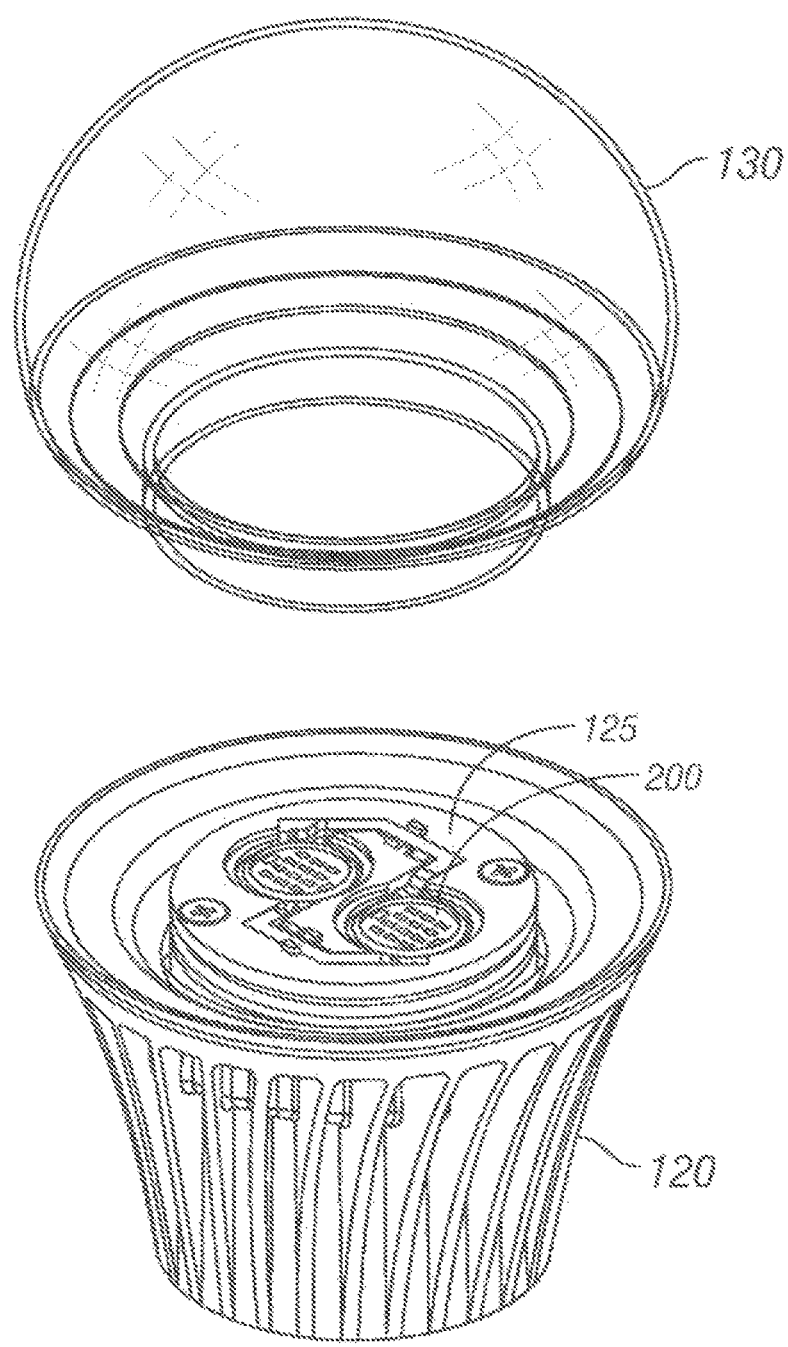
FIG. 7 is an exploded view of a portion of the LED lamp of FIG. 2.

As shown in FIG. 5, heat sink 120 is disposed about housing 115. As shown in FIG. 6, two LED chips 200 are mounted onto a support surface (or directly to heat sink 120), and maintained in place by holder 125. While two LED chips 200 are shown, alternative embodiments may include any number of LED chips (i.e., one or more), or any number of LED dies individually mounted. Screws 129 are used to secure holder 125 to heat sink 120. Screws 129 may be any screws known in the art. Spring wire connectors 127 are used to connect LED chips 200 to the driver circuit 440 on PCB 117. In an alternative embodiment, LED chips 200 (with or without packaging) may be attached directly to heat sink 120 without the use of holder 125, screws 129, or connectors 127. As shown in FIG. 7, optic 130 is then mounted on and attached to heat sink 120.

Figure 8:
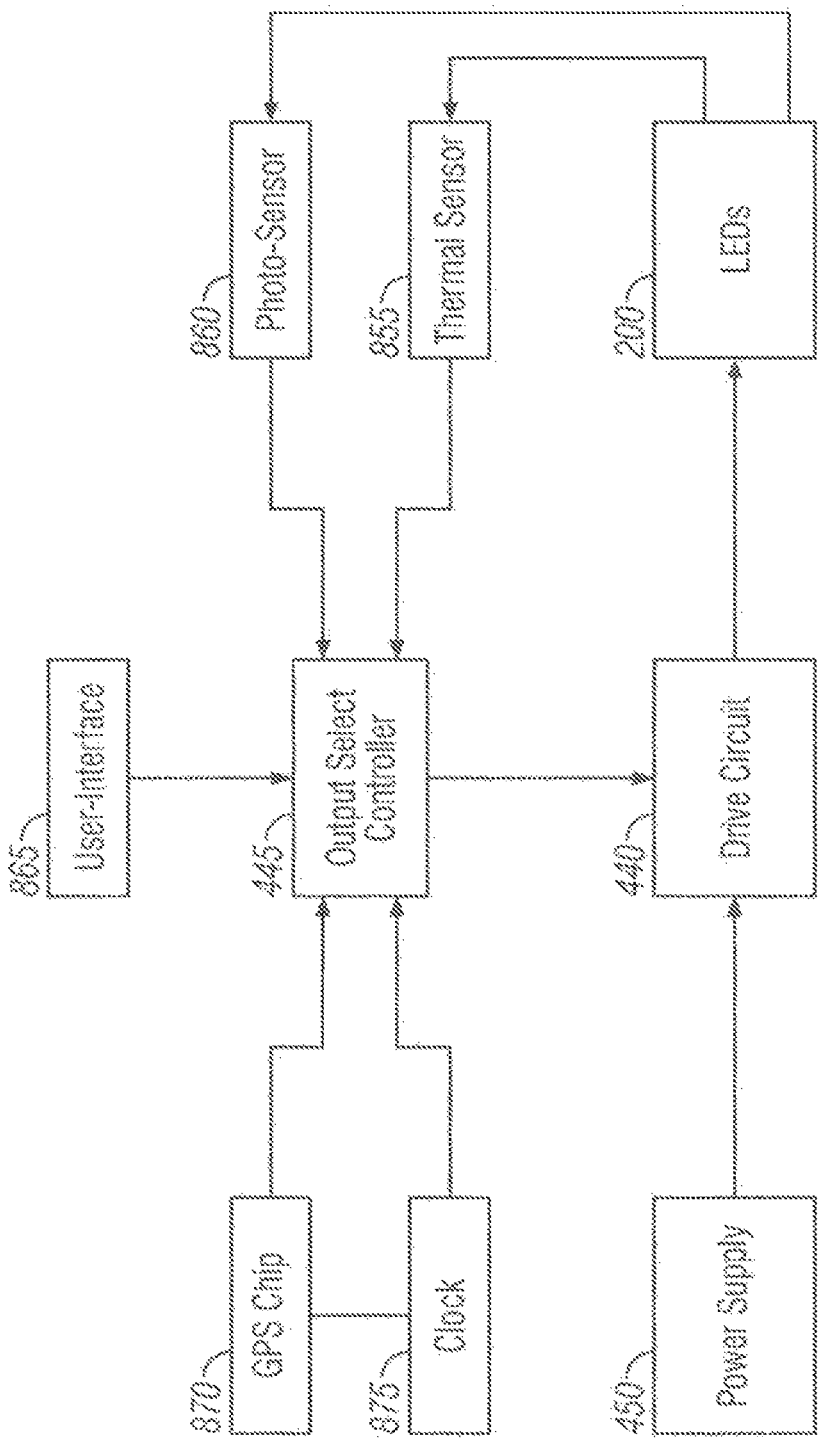
FIG. 8 is a schematic process diagram of an LED lamp in accordance with the present invention.

FIG. 8 is a schematic process diagram of an LED lamp in accordance with the present invention. FIG. 8 also serves a depiction of the functional components mounted on PCB 117, or otherwise associated with LED lamp 100. In practice, a power supply 450 is used to provide power to driver circuit 440. Power supply 450 may, for example, convert AC power to DC power, for driving the LED dies. Driver circuit 440 receives power input from power supply 450, and directional input from output-select controller 445. In turn, driver circuit 440 provides the appropriate current supply to drive the LED dies in accordance with the desired spectral output. Controller 445 therefore serves to control the driving of LEDs 200, and may control light output based on factors such as: time of day, ambient light, real time input, temperature, optical output, location of lamp, etc.

Variations in temperature during operation can cause a spectral shift of individual dies. In an embodiment, a photosensor 860 is included to monitor the light output of the LEDs 200 to insure consistency and uniformity. Monitoring the output of LEDs 200 allows for real time feedback and control of each die to maintain the desired output spectrum. Photosensor 860 may also be used to identify the ambient light conditions. Photo-sensor 860 thus provides an input to controller 445.

In another embodiment, a thermal sensor 855 is used to measure the temperature of the LED dies and/or board supporting the LED dies. Because the light output of the dies is a known function of temperature, the measured temperature can be used to determine the light output of each die. Thermal sensor 855 may also be used to measure the ambient temperature conditions. Thermal sensor 855 thus provides another input to controller 445.

In another embodiment, a GPS chip 870 and/or clock 875 is included and interfaced with controller 445. Because lamps are shipped around the world to their end location, the ability to determine the expected/actual ambient light, daily light cycle, and seasonal light cycle variations is important in any lamp that may generate light to stimulate or alter circadian rhythms. GPS chip 870 and/or clock 875 provide inputs into controller 445 such that the time of day, seasonality, and other factors can be taken into account by controller 445 to control the lamp output accordingly. For example, by knowing the time of day based on location, the pre-sleep spectrum of the lamp can be generated during the later hours of the day.

In still another embodiment, a user-interface 865 is provided to allow a user to select the desired configuration. User-interface 865 may be in the form of a knob, switch, digital input, or equivalent means. As such, user-interface 865 provides an additional input to controller 445.

In one embodiment, the pre-sleep configuration spectrum includes a portion of the spectrum that is reduced (e.g., notched/troughed) in intensity. This trough is centered at about 470 nm (or alternatively between about 470-480 nm, between about 460-480 nm, between about 470-490 nm, or between about 460-490 nm). Such wavelength ranges may be the most important contributor to, and most effective at, suppressing melatonin. Thus minimizing exposure in such wavelength bands during pre-sleep phase will be efficacious. In one embodiment, the notching of the pre-sleep spectrum is obtained using a phosphor-coated mint LED having a specific output spectrum to accomplish the notch in the pre-sleep spectrum. The mint LED itself may include a notch/trough with a minimum in the 470-480 nm (or 460-490 nm range), and may be characterized by a maximum intensity in these wavelength ranges as a fractional percent of the peak intensity of the mint LED (e.g., the maximum of 470-480 emission is less than about 2.5% of the peak intensity; the max between about 460-490 nm is less than about 5% of the peak intensity).

With reference again to FIG. 9, illustrated is a relative radiant power curve for a mint LED die used in one embodiment presented. As used herein, the terms "mint LED" or "mint LED die" or "mint die" should be construed to include any LED source, LED chip, LED die (with or without photo-conversion material on the die), or any equivalent light source that is configured or capable of producing the relative radiant power curve shown in FIG. 9, or a relative radiant power curve equivalent thereto. Of particular interest to the shown relative radiant power curve is the spectral "notch" between about 460-490 nm, and more specifically between at about 470-480 nm. Said spectral notch provides a relative intensity, with respect to the peak intensity, that allows the combination of LED dies (or equivalent light sources) to achieve their desired results (i.e., the desired output configuration). In one embodiment, the maximum intensity of the mint LED between about 460-490 nm is less than about 5% of the peak intensity. In alternative embodiments the maximum intensity of the mint LED between about 460-490 nm is less than about 7.5%, or about 10%, or about 15%, or about 20% of the peak intensity.

Further, in one embodiment, the maximum intensity of the mint LED between about 470-480 nm is less than about 2.5% of the peak intensity. In alternative embodiments, the maximum intensity of the mint LED between about 470-480 nm is less than about 3.5%, 5%, 10%, or 20% of the peak intensity.

Figure 12:
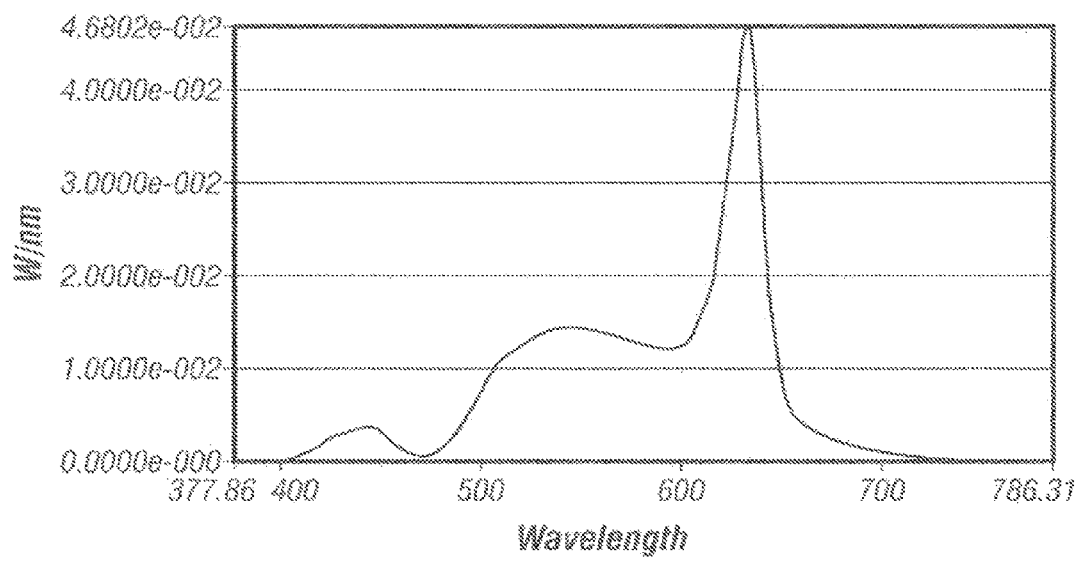
FIG. 12 shows a power spectral distribution of an LED lamp III a pre-sleep configuration, in accordance with another embodiment presented.
Figure 13:
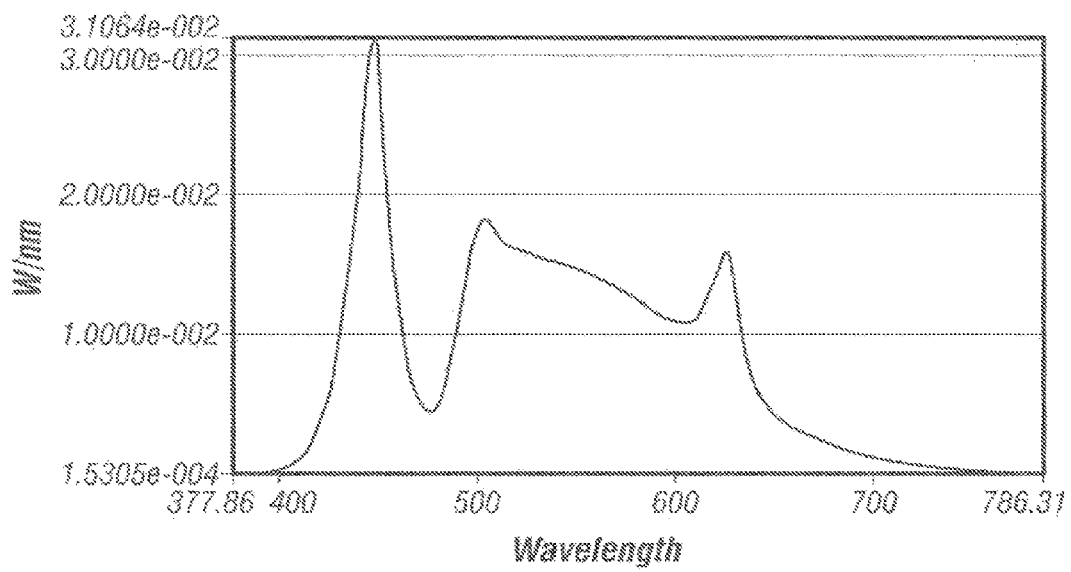
FIG. 13 shows a power spectral distribution of an LED lamp in a phase-shift configuration, in accordance with one embodiment presented.
Figure 14:
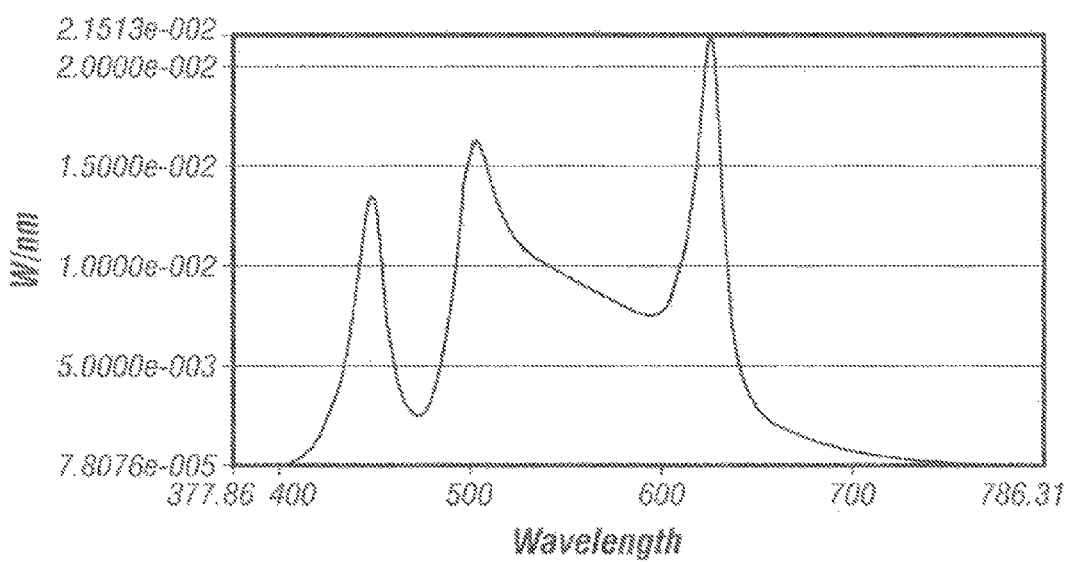
FIG. 14 shows a power spectral distribution of an LED lamp in a general lighting configuration, in accordance with one embodiment presented.

FIGS. 12, 13, and 14 show the power spectral distributions corresponding respectively to the pre-sleep, phase-shift, and general illumination configurations of the LED lamp in accordance with one embodiment of the invention. The LED lamp in this embodiment comprises an LED board with a ratio of Cyan, Mint, Red, and Royal Blue dies of 3:3:2:1 respectively. The spectral output of the lamp according to each configuration is adjusted by generating radiant fluxes from multiple dies as described below.

FIG. 12 shows a power spectral distribution of an LED lamp III a pre-sleep configuration, in accordance with another embodiment presented. The pre-sleep configuration shown in FIG. 13 is produced by an array of LED dies in the 3:3:2:1 ratio, driven as follows: (1) three cyan LEDs driven at 7.65V, 66 mA, 0.16679 radiant flux; (2) three mint LEDs driven parallel at 11.13V, 95 1mA, 1.8774 radiant flux; (3) two red-orange LEDs driven at 4.375V, 998 mA, 0.96199 radiant flux; and (4) one royal blue LED driven at 2.582V, 30 mA, 0.0038584 radiant flux. The total luminous flux is 1.024e+003 1 m. The total radiant flux is 3.0238e+000 W. The dominant wavelength is 580.3 nm. The general CRI is 87.30. The color temperature is 2871 K. The 1931 Coordinates (2°) are x: 0.4649, y: 0.4429. The luminous power per radiant watt is 338 lumens per radiant watt.

FIG. 13 shows a power spectral distribution of an LED lamp in a phase-shift configuration, in accordance with one embodiment presented. The phase-shift configuration shown in FIG. 14 is produced by an array of LED dies in the 3:3:2:1 ratio, driven as follows: (1) three cyan LEDs driven at 8.19V, 235 mA, 0.47233 radiant flux; (2) three mint LEDs driven parallel at 11.14V, 950 mA, 1.9047 radiant flux; (3) two red-orange LEDs driven at 3.745V, 147 mA, 0.1845 radiant flux; and (4) one royal blue LED driven at 2.802V, 525 mA, 0.69093 radiant flux. The total luminous flux is 9.87ge+002 1 m. The total radiant flux is 3.2138e+000 W. The dominant wavelength is 495.6 nm. The peak wavelength is 449.7 nm. The general CRI is 87.42. The color temperature is 6,599 K. The 1931 Coordinates (2°) are x: 0.3092, y: 0.3406. The luminous power per radiant watt is 307 lumens per radiant watt.

In an alternative embodiment, in the phase-shift configuration, the intensity levels of blue component in the 455 nm to 485 nm range is preferably greater than about 125% of the relative spectral power of any other peaks in the visible light spectrum higher than 485 nm. In alternative embodiments, the blue component in the 455 nm to 485 nm range may be is preferably greater than about 150%; or about 175%; or about 200%; or about 250%; or about 300% of the relative spectral power of any other peaks in the visible light spectrum higher than 485 nm. The color rendering index is preferably greater than 80. By varying the radiant fluxes of one or more of the dies, for example by varying the current drawn by the dies, the intensity of the blue component relative to other spectral peaks greater than 485 nm may be adjusted to the desired level.

Figure 15:
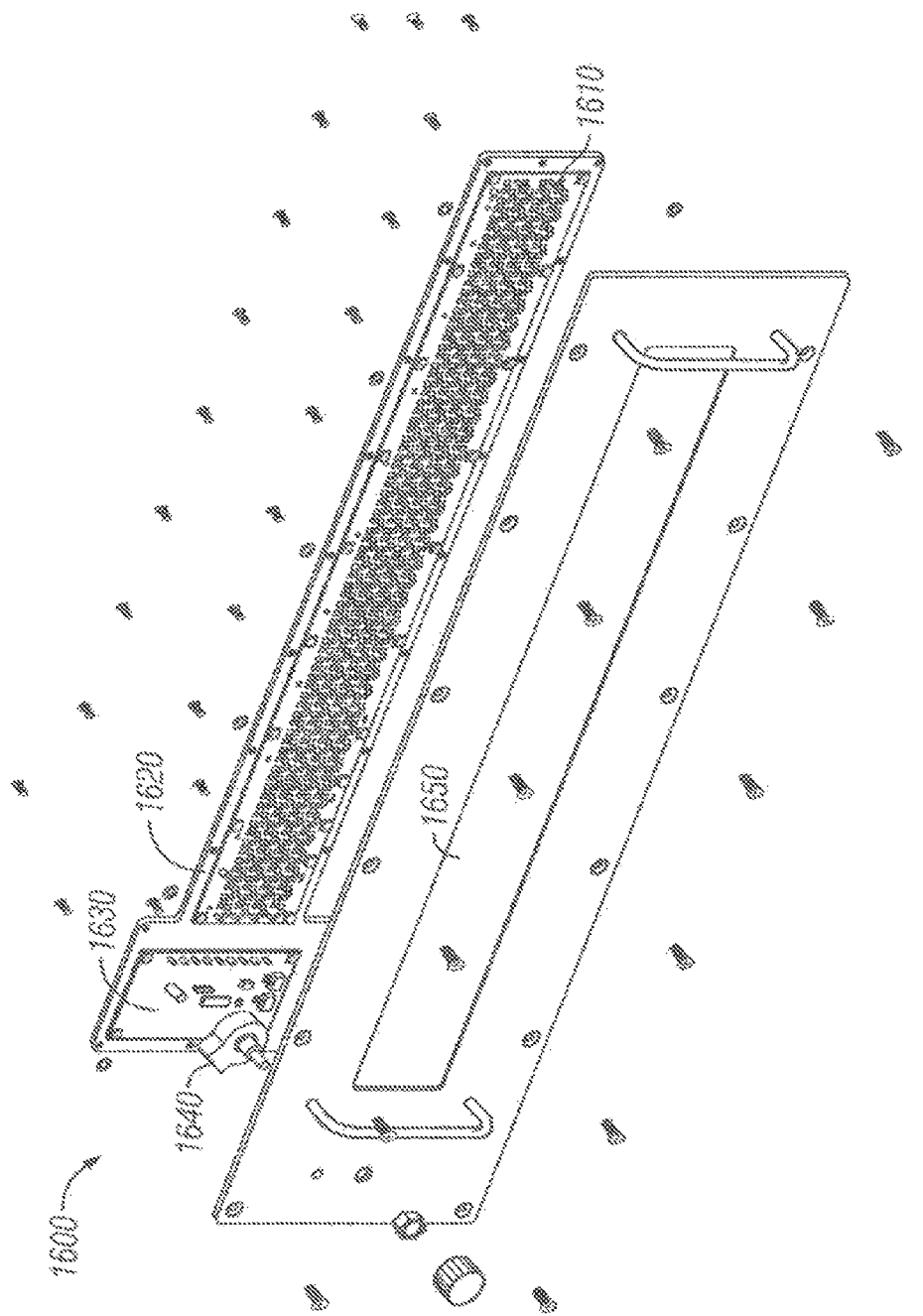
FIG. 15 is an exploded view of an LED lamp in accordance with another embodiment presented.

FIG. 14 shows a power spectral distribution of an LED lamp in a general lighting configuration, in accordance with one embodiment presented. The general lighting configuration shown in FIG. 15 is produced by an array of LED dies in the 3::3:2:1 ratio, driven as follows: (1) three cyan LEDs driven at 8.22V, 211 mA, 0.44507 radiant flux; (2) three mint LEDs driven parallel at 10.06V, 499 mA, 1.1499 radiant flux;

(3) two red-orange LEDs driven at 3.902V, 254 mA, 0.34343 radiant flux; and (4) one blue LED driven at 2.712V, 190 mA, 0.27280 radiant flux. The total luminous flux is 7.192e+002 1 m. The total radiant flux is 2.2248e+000 W. The dominant wavelength is 566.2 nm. The peak wavelength is 625.9 nm. The general CRI is 93.67. The color temperature is 4897 K. The 1931 Coordinates (2°) are x: 0.3516, y: 0.3874. The luminous power per radiant watt is 323 lumens per radiant watt.

In an alternative embodiment, in the general illumination configuration, the intensity levels of blue component in the 380 nm to 485 nm range is preferably about 100% of the relative spectral power of any other peaks in the visible light spectrum higher than 485 nm. In alternative embodiments, the intensity levels of blue component in the 380 nm to 485 nm range is preferably less than about 100%; or less than about 90%; or less than about 80%; or between about 20% to about 100% of the relative spectral power of any other peaks in the visible light spectrum higher than 485 nm. The color rendering index is preferably greater than 85.

FIG. 15 is an exploded view of an LED lamp in accordance with another embodiment presented. FIG. 15 shows an additional form factor in which the present invention may be applied. For example, FIG. 15 shows a lamp 1600 having an array of LEDs 1610. The LEDs 1610 may be provided in the 3:3:2:1 ratio of cyan:mint:red--orange:blue, as described above.

In another embodiment, the LEDs 1610 may be provided in a 3:3:2:3 ratio of cyan:mint:red:blue, as described above. The LEDs are mounted on a support frame 1620, which may serve as a heat-sink. LED circuitry 1630 is used to drive the LEDs 1610 with appropriate drive currents to achieve two or more output configurations (e.g., pre-sleep, phase-shift, and general lighting configurations). An output-select controller 1640 (and associated knob) are provided to allow an end-user to select the desired output configuration. An optic 1650 is provided in front of the LEDs 1610 to provide diffusive effects. The form factor may be completed by fastening the components with means such as screws and/or nuts and bolts, as shown.

Additional Embodiments

Figure 16:
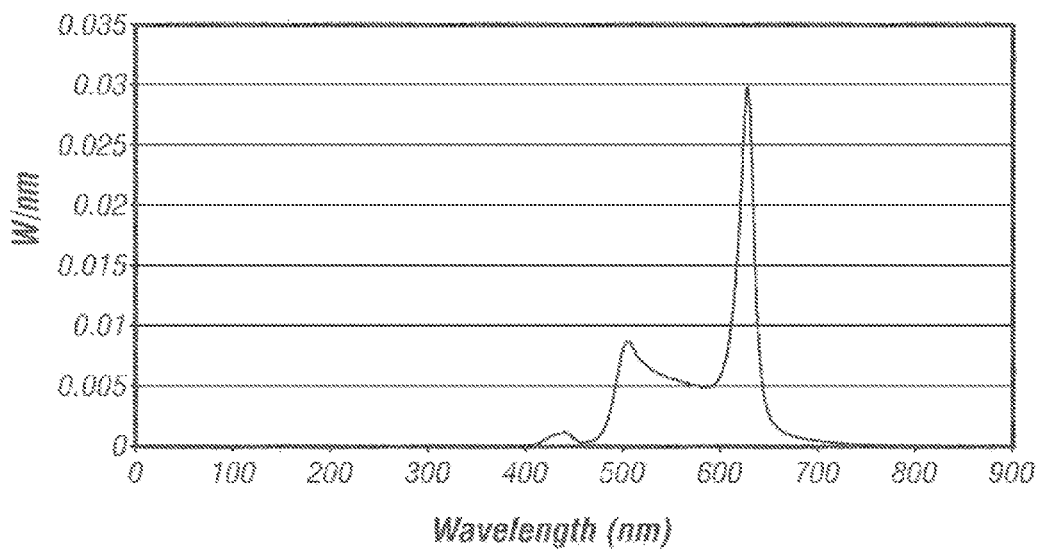
FIG. 16 shows an alternative power spectral distribution for an LED lamp in a pre-sleep configuration.
Figure 17:
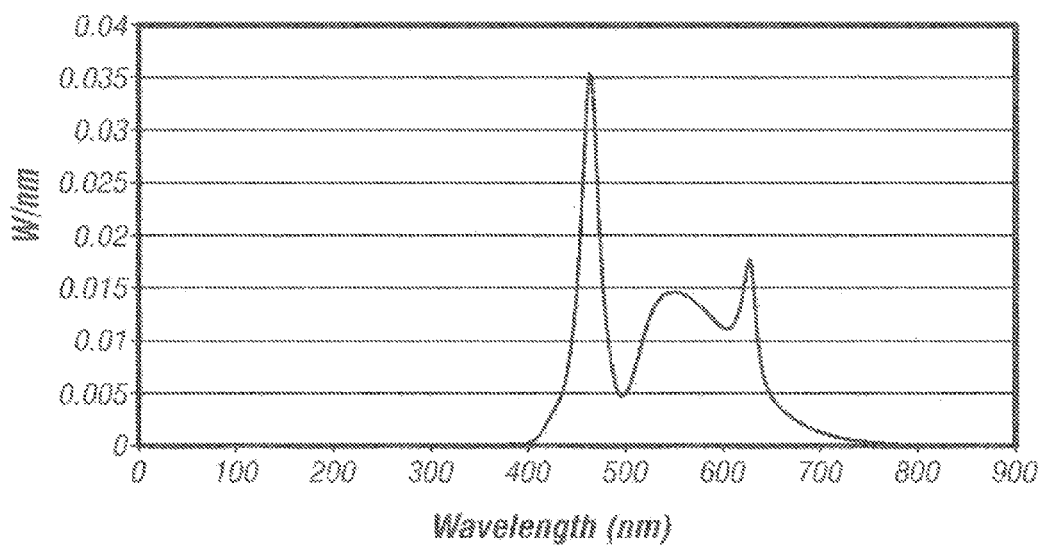
FIG. 17 shows an alternative power spectral distribution for an LED lamp in a phase-shift configuration.
Figure 18:
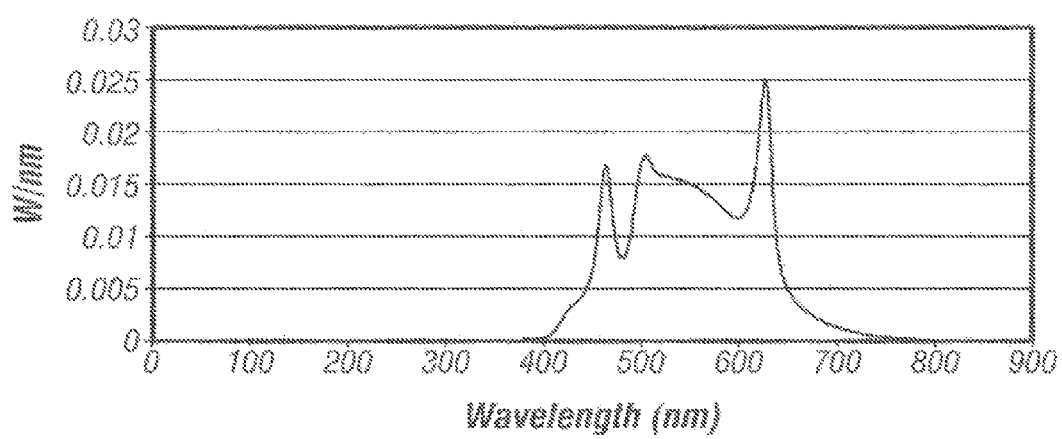
FIG. 18 shows an alternative power spectral distribution for an LED lamp in a general lighting configuration.

FIGS. 16, 17, and 18 show the power spectral distributions corresponding respectively to the pre-sleep, phase-shift, and general illumination configurations of the LED lamp in accordance with one embodiment of the invention. The LED lamp in this embodiment comprises an LED board with a ratio of Cyan, Mint, Red, and Blue dies of 3:3:2:3 respectively. The spectral output of the lamp according to each configuration is adjusted by generating radiant fluxes from multiple dies as described below.

FIG. 16 shows a power spectral distribution of an LED lamp III a pre-sleep configuration, in accordance with another embodiment presented. The pre-sleep configuration shown in FIG. 13 is produced by an array of LED dies in the 3:3:2:3 ratio, driven as follows: (1) three cyan LEDs driven at 7.83V, 91 mA, to generate 0.2048 radiant watts; (2) three mint LEDs driven parallel at 9.42V, 288 mA, 0.6345 radiant watts; (3) two red-orange LEDs driven at 4.077V, 490 mA, 0.5434 radiant watts. The dominant wavelength is 581.4 nm. The general CRI is 71. The color temperature is 2719 K. The luminous power per radiant watt is 331 lumens per radiant watt. The efficacy is 91 lumens per watt.

FIG. 17 shows a power spectral distribution of an LED lamp in a phase-shift configuration, in accordance with another embodiment presented. The phase-shift configuration shown in FIG. 18 is produced by an array of LED dies in the 3:3:2:3 ratio, driven as follows: (1) three mint LEDs driven parallel at 11.27V, 988 mA, 1.679 radiant watts; (2) two red-orange LEDs driven at 3.78V, 180 mA, 1.971 radiant, and (3) three blue LEDs driven at 9.07V, 296 mA, 0.8719 radiant watts. The dominant wavelength is 476.9 nm. The general CRI is 88. The color temperature is 6235 K. The luminous power per radiant watt is 298 lumens per radiant watt. The efficacy is 63 lumens per watt.

FIG. 18 shows a power spectral distribution of an LED lamp in a general lighting configuration, in accordance with another embodiment presented. The general lighting configuration shown in FIG. 19 is produced by an array of LED dies in the 3:3:2:3 ratio, driven as follows: (1) three cyan LEDs driven at 8.16V, 218 mA, to generate 0.4332 radiant watts; (2) three mint LEDs driven parallel at 11.23V, 972 mA, 1.869 radiant watts; (3) two red-orange LEDs driven at 3.89V, 295 mA, 0.3520 radiant watts. The dominant wavelength is 565.6 nm. The general CRI is 90. The color temperature is 4828 K. The luminous power per radiant watt is 335 lumens per radiant watt. The efficacy is 68 lumens per watt In another embodiment, there is provided a tunable LED lamp for producing a biologically-adjusted light output with a color rendering index above 70. The LED lamp comprises: a base; a housing attached to the base; a power circuit disposed within the housing and having electrical leads attached to the base; a driver circuit disposed within the housing and electrically coupled to the power circuit; and a heat sink disposed about the housing. The LED lamp further comprises: a plurality of LED dies mounted on a support coupled to the housing, wherein each of the plurality of LED dies is electrically coupled to and driven by the driver circuit. The plurality of LED dies includes two red LED dies, three cyan LED dies, four mint LED dies, and three blue LED dies. The LED lamp further comprises: an output-select controller electrically coupled to the driver circuit to program the driver circuit to drive the LED dies in one of a plurality of light output configurations. The plurality of light output configurations includes a pre-sleep configuration, a phase-shift configuration, and a general lighting configuration.

The output-select controller may include a user-input interface allowing a user to select the light output configuration. The LED lamp my further include an input sensor electrically coupled to the output-select controller to provide an input variable for consideration in the selection of the light output configuration. The input sensor may be a thermal sensor, a photo-sensor, and/or a GPS chip. The input variable may be selected from the group consisting of: an ambient temperature, a support temperature, an LED die temperature, a housing temperature, the light output produced by the lamp, an ambient light, a daily light cycle, a location of the lamp, an expected ambient light, a seasonal light cycle variation, a time of day, and any combinations and/or equivalents thereof.

In the pre-sleep configuration, the driver circuit drives the plurality of LED dies such that a blue output intensity level, in a visible spectral output range of between about 380 nm and about 485 nm, is less than about 10% of a relative spectral power of any other peaks in the visible spectral output above about 485 nm. For example, the driver circuit may drive the plurality of LED dies such that about 150 mA of current is delivered to the mint LED dies; about 360 mA of current is delivered to the red LED dies; and about 40 mA of current is delivered to the cyan LED dies.

In the phase-shift configuration, the driver circuit drives the plurality of LED dies such that a blue output intensity level, in a visible spectral output range of between about 455 nm and about 485 nm, is greater than about 125% of a relative spectral power of any other peaks in the visible spectral output above about 485 nm. The color rendering index in the phase-shift configuration may be greater than 80. For example, the driver circuit may drive the plurality of LED dies such that about 510 mA of current is delivered to the mint LED dies; about 1800 mA of current is delivered to the red LED dies; about 40 mA of current is delivered to the cyan LED dies; and about 100 mA of current is delivered to the blue LED dies.

In the general lighting configuration, the driver circuit drives the plurality of LED dies such that a blue output intensity level, in a visible spectral output range of between about 380 nm and about 485 nm, is between about 100% to about 20% of a relative spectral power of any other peaks in the visible spectral output above about 485 nm. The color rendering index in the general lighting configuration may be greater than 85. For example, the driver circuit may drive the plurality of LED dies such that about 450 mA of current is delivered to the mint LED dies; about 230 mA of current is delivered to the red LED dies; about 110 mA of current is delivered to the cyan LED dies; and about 60 mA of current is delivered to the blue LED dies.

In another embodiment, there is provided an LED lamp, comprising: a housing; a driver circuit disposed within the housing and configured to electrically couple to a power source; and a plurality of LED dies mounted on a support coupled to the housing, wherein each of the plurality of LED dies is electrically coupled to and driven by the driver circuit. The LED lamp further includes an output-select controller electrically coupled to the driver circuit to program the driver circuit to drive the LED dies in one of a plurality of light output configurations. The output-select controller may also include a user-input interface allowing a user to select the light output configuration.

The plurality of light output configurations includes a pre-sleep configuration and a general lighting configuration. The plurality of light output configurations may further include a phase-shift configuration. The plurality of LED dies may include red LED dies, cyan LED dies, mint LED dies, and blue LED dies. The ratio of red LED dies to cyan LED dies to mint LED dies to blue LED dies of 2:3:4:3, respectively. The LED lamp may be tunable to produce a biologically-adjusted light output with a color rendering index above 70.

The LED lamp may further comprise an input sensor electrically coupled to the output-select controller to provide an input variable for consideration in the selection of the light output configuration. The input sensor may be a thermal sensor, a photo-sensor, and/or a GPS chip. The input variable may be selected from the group consisting of: an ambient temperature, a support temperature, an LED die temperature, a housing temperature, the light output produced by the lamp, an ambient light, a daily light cycle, a location of the lamp, an expected ambient light, a seasonal light cycle variation, a time of day, and any combinations and/or equivalents thereof.

In the pre-sleep configuration, the driver circuit drives the plurality of LED dies such that a blue output intensity level, in a visible spectral output range of between about 380 nm and about 485 nm, is less than about 10% of a relative spectral power of any other peaks in the visible spectral output above about 485 nm. For example, the driver circuit may drive the plurality of LED dies such that about 150 mA of current is delivered to the mint LED dies; about 360 mA of current is delivered to the red LED dies; and about 40 mA of current is delivered to the cyan LED dies.

In the phase-shift configuration, the driver circuit drives the plurality of LED dies such that a blue output intensity level, in a visible spectral output range of between about 455 nm and about 485 nm, is greater than about 125% (or greater than about 150%; or greater than about 200%) of a relative spectral power of any other peaks in the visible spectral output above about 485 nm. The color rendering index in the phase-shift configuration may be greater than 80. For example, the driver circuit may drive the plurality of LED dies such that about 510 mA of current is delivered to the mint LED dies; about 180 mA of current is delivered to the red LED dies; about 40 mA of current is delivered to the cyan LED dies; and about 100 mA of current is delivered to the blue LED dies In the general lighting configuration, the driver circuit drives the plurality of LED dies such that a blue output intensity level, in a visible spectral output range of between about 380 nm and about 485 nm, is between about 100% to about 20% of a relative spectral power of any other peaks in the visible spectral output above about 485 nm. The color rendering index in the general lighting configuration may be greater than 85. For example, the driver circuit may drive the plurality of LED dies such that about 450 mA of current is delivered to the mint LED dies; about 230 mA of current is delivered to the red LED dies; about 110 mA of current is delivered to the cyan LED dies; and about 60 mA of current is delivered to the blue LED dies.

In another embodiment, there is provided a tunable LED lamp for producing a biologically-adjusted light output with a color rendering index above 70, comprising: a base; a housing attached to the base; a power circuit disposed within the housing and having electrical leads attached to the base; a driver circuit disposed within the housing and electrically coupled to the power circuit; a heat sink disposed about the housing; a plurality of LED dies mounted on a support coupled to the housing, wherein each of the plurality of LED dies is electrically coupled to and driven by the driver circuit, and wherein the plurality of LED dies includes a ratio of two red-orange LED dies to three cyan LED dies to three mint LED dies to one blue LED dies; and an output-select controller electrically coupled to the driver circuit to program the driver circuit to drive the LED dies in one of a plurality of light output configurations, wherein the plurality of light output configurations includes a pre-sleep configuration, a phase-shift configuration, and a general lighting configuration. In the pre-sleep configuration, the driver circuit may drive the plurality of LED dies such that about 950 mA of current is delivered to the mint LED dies, about 1,000 mA of current is delivered to the red-orange LED dies, about 65 mA of current is delivered to the cyan LED dies; and about 30 mA of current is delivered to the blue LED dies. In the phase-shift configuration, the driver circuit may drive the plurality of LED dies such that about 950 mA of current is delivered to the mint LED dies, about 150 mA of current is delivered to the red-orange LED dies, about 235 mA of current is delivered to the cyan LED dies, and about 525 mA of current is delivered to the blue LED dies. In the general lighting configuration, the driver circuit may drive the plurality of LED dies such that about 500 mA of current is delivered to the mint LED dies, about 250 mA of current is delivered to the red-orange LED dies, about 210 mA of current is delivered to the cyan LED dies, and about 190 mA of current is delivered to the blue LED dies. In other embodiments, alternative currents may be delivered to vary the radiant fluxes and achieve the desired spectral output.

In yet another embodiment, there is provided a method of manufacturing a tunable LED lamp for producing a biologically-adjusted light output with a color rendering index above 70. The method comprises: (a) attaching a base to a housing; (b) electrically coupling leads of a power circuit within the housing to the base; (c) electrically coupling a driver circuit disposed within the housing to the power circuit; (d) mounting a plurality of LED dies on a support coupled to the housing such that each of the plurality of LED dies is electrically coupled to and driven by the driver circuit, and wherein the plurality of LED dies includes two red LED dies, three cyan LED dies, four mint LED dies, and three blue LED dies; and (e) configuring the driver circuit to drive the LED dies in one of a plurality of light output configurations, wherein the plurality of light output configurations includes a pre-sleep configuration, a phase-shift configuration, and a general lighting configuration.

The method may further comprise: (f) configuring the driver circuit to drive the plurality of LED dies such that a blue output intensity level, in a visible spectral output range of between about 380 nm and about 485 nm, is less than about 10% of a relative spectral power of any other peaks in the visible spectral output above about 485 nm; (g) configuring the driver circuit to drive the plurality of LED dies such that a blue output intensity level, in a visible spectral output range of between about 455 nm and about 485 nm, is greater than about 125% of a relative spectral power of any other peaks in the visible spectral output above about 485 nm; and/or (h) configuring the driver circuit to drive the plurality of LED dies such that a blue output intensity level, in a visible spectral output range of between about 380 nm and about 485 nm, is between about 100% to about 20% of a relative spectral power of any other peaks in the visible spectral output above about 485 nm.

The method may further comprise: (i) configuring the driver circuit to drive the plurality of LED dies such that about 150 mA of current is delivered to the mint LED dies, about 360 mA of current is delivered to the red LED dies, and about 40 mA of current is delivered to the cyan LED dies; (j) configuring the driver circuit to drive the plurality of LED dies such that about 510 mA of current is delivered to the mint LED dies, about 180 mA of current is delivered to the red LED dies, about 40 mA of current is delivered to the cyan LED dies, and about 100 mA of current is delivered to the blue LED dies; and/or (k) configuring the driver circuit to drive the plurality of LED dies such that about 450 mA of current is delivered to the mint LED dies, about 230 mA of current is delivered to the red LED dies, about 110 mA of current is delivered to the cyan LED dies, and about 60 mA of current is delivered to the blue LED dies.

In another embodiment, there is provided an LED lamp comprising a housing, a driver circuit disposed within the housing and configured to electrically couple to a power source, and a plurality of LED dies mounted on a support coupled to the housing. Each of the plurality of LED dies may be electrically coupled to and driven by the driver circuit; and an output-select controller electrically coupled to the driver circuit to program the driver circuit to drive the LED dies in one of a plurality of light output configurations, wherein the plurality of light output configurations includes a pre-sleep configuration and a general lighting configuration. The plurality of LED dies includes red-orange LED dies, cyan LED dies, mint LED dies, and blue LED dies. The plurality of LED dies includes a ratio of red-orange LED dies to cyan LED dies to mint LED dies to blue LED dies of 2:3:3:1, respectively.

In another embodiment, there is provided a method of manufacturing a tunable LED lamp for producing a biologically-adjusted light output with a color rendering index above 70, comprising: attaching a base to a housing; electrically coupling leads of a power circuit within the housing to the base; electrically coupling a driver circuit disposed within the housing to the power circuit; mounting a plurality of LED dies on a support coupled to the housing such that each of the plurality of LED dies is electrically coupled to and driven by the driver circuit, and wherein the plurality of LED dies includes two red-orange LED dies, three cyan LED dies, three mint LED dies, and one blue LED dies; and configuring the driver circuit to drive the LED dies in one of a plurality of light output configurations, wherein the plurality of light output configurations includes a pre-sleep configuration, a phase-shift configuration, and a general lighting configuration. In the pre-sleep configuration the method may further comprises configuring the driver circuit to drive the plurality of LED dies such that about 950 mA of current is delivered to the mint LED dies, about 1,000 mA of current is delivered to the red-orange LED dies, about 65 mA of current is delivered to the cyan LED dies, and about 30 mA of current is delivered to the blue LED dies. In the phase-shift configuration the method may further comprise: configuring the driver circuit to drive the plurality of LED dies such that about 950 mA of current is delivered to the mint LED dies, about 150 mA of current is delivered to the red LED dies, about 235 mA of current is delivered to the cyan LED dies, and about 525 mA of current is delivered to the blue LED dies. In the general lighting configuration the method may further comprise: configuring the driver circuit to drive the plurality of LED dies such that about 500 mA of current is delivered to the mint LED dies, about 250 mA of current is delivered to the red LED dies, about 210 mA of current is delivered to the cyan LED dies, and about 190 mA of current is delivered to the blue LED dies.

It will be evident to those skilled in the art, that other die configuration or current schemes may be employed to achieve the desired spectral output of the LED lamp for producing biologically adjusted light.

In another embodiment, there is provided an LED lamp comprising a housing, a driver circuit disposed within the housing and configured to electrically couple to a power source, and a plurality of LED dies mounted on a support coupled to the housing. Each of the plurality of LED dies may be electrically coupled to and driven by the driver circuit. The plurality of LED dies may include mint LED dies, hyper red LED dies, and blue LED dies. In some embodiments, the plurality of LED dies includes a ratio of mint LED dies to hyper red LED dies to blue LED dies of 15:5:4, respectively.

In some embodiments, all of the plurality of LED dies may be serially connected. Furthermore, the drive circuit may be configured to operate the plurality of LED dies such that a relative peak intensity of light emitted by the blue LED dies is within the range from 90% to 100% of a peak intensity of light emitted by the hyper red LED dies and a relative peak intensity of light emitted by the mint LED dies is within the range from 50% to 60% of the peak intensity of light emitted by the hyper red LED dies.

Additionally, the drive circuit may be configured to operate the plurality of LED dies to emit light having a color temperature of at least 6,200 K. More specifically, the drive circuit may be configured to operate the plurality of LED dies to emit light having a color temperature of 6,240 K.

Additionally, the drive circuit may be configured to operate the plurality of LED dies to emit light having a color rendering index of at least 90. More specifically, the drive circuit may be configured to operate the LED dies to have a color rendering index of 92.2.

In another embodiment, there is provided an LED lamp comprising a housing, a driver circuit disposed within the housing and configured to electrically couple to a power source, and a plurality of LED dies mounted on a support coupled to the housing. Each of the plurality of LED dies may be electrically coupled to and driven by the driver circuit. The plurality of LED dies may include mint LED dies, hyper red LED dies, and blue LED dies. In some embodiments, the plurality of LED dies includes a ratio of mint LED dies to hyper red LED dies to blue LED dies of 1:1:1, respectively. Furthermore, the plurality of LED dies may comprise 7 mint LED dies, 7 hyper red LED dies, and 7 blue LED dies.

In some embodiments, each of the like-colored LED dies may be serially connected. That is to say, the mint LED dies may be serially connected, the hyper red LED dies may be serially connected, and the blue LED dies may be serially connected. Furthermore, the drive circuit may be configured to direct power to the various serially-connected LED dies unequally. In some embodiments, the driver circuit may deliver power to the plurality of LED dies in a ratio of 6.9 watts to the mint LED dies, 3.2 watts to the hyper red LED dies, and 2.0 watts to the blue LED dies.

In some embodiments, the drive circuit may be configured to operate the plurality of LED dies such that a relative peak intensity of light emitted by the blue LED dies is within the range from 80% to 90% of a peak intensity of light emitted by the hyper red LED dies and a relative peak intensity of light emitted by the mint LED is within the range from 30% to 40% of the peak intensity of light emitted by the hyper red LED dies.

Additionally, the drive circuit may be configured to operate the plurality of LED dies to emit light having a color temperature of at least 6,200 K. More specifically, the drive circuit may be configured to operate the plurality of LED dies to emit light having a color temperature of 6,202 K.

Additionally, the drive circuit may be configured to operate the plurality of LED dies to emit light having a color rendering index of at least 90. More specifically, the drive circuit may be configured to operate the LED dies to have a color rendering index of 91.3.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiment of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

That which is claimed is:

1. A tuned LED lamp comprising:
a housing;
a drive circuit disposed within the housing and configured to electrically couple to a power source; and
a plurality of LED dies mounted on a support coupled to the housing, wherein each of the plurality of LED dies is electrically coupled to and driven by the drive circuit;
wherein the plurality of LED dies comprises mint, hyper red, and blue LED dies in a ratio of:
15 mint LED dies, to
5 hyper red LED dies, to
4 blue LED dies; and
wherein the drive circuit is configured to operate the plurality of LED dies to emit light that selectively increases or decreases melatonin suppression in an observer of the emitted light.

2. The tuned LED lamp according to claim 1 wherein the plurality of LED dies is serially connected.

3. The tuned LED lamp according to claim 1 wherein the drive circuit is configured to operate the plurality of LED dies such that a relative peak intensity of light emitted by the blue LED dies is within the range from 90% to 100% of a peak intensity of light emitted by the hyper red LED dies and a relative peak intensity of light emitted by the mint LED dies is within the range from 50% to 60% of the peak intensity of light emitted by the hyper red LED dies.

4. The tuned LED lamp according to claim 1 wherein the drive circuit is configured to operate the plurality of LED dies to emit light having a color temperature of at least 6,200 K.

5. The tuned LED lamp according to claim 1 wherein the drive circuit is configured to operate the plurality of LED dies to emit light having a color rendering index of at least 90.

6. A tuned LED lamp comprising:
a housing;
a drive circuit disposed within the housing and configured to electrically couple to a power source; and
a plurality of LED dies mounted on a support coupled to the housing, wherein each of the plurality of LED dies is electrically coupled to and driven by the drive circuit;
wherein the plurality of LED dies comprises mint, hyper red, and blue LED dies in a ratio of:
1 mint LED die, to
1 hyper red LED die, to
1 blue LED die; and
wherein the drive circuit is configured to operate the plurality of LED dies to emit light that selectively increases or decreases melatonin suppression in an observer of the emitted light.

7. The tuned LED lamp according to claim 6 wherein the drive circuit is configured to operate the plurality of LED dies such that a relative peak intensity of light emitted by the blue LED dies is within the range from 80% to 90% of a peak intensity of light emitted by the hyper red LED dies and a relative peak intensity of light emitted by the mint LED dies is within the range from 30% to 40% of the peak intensity of light emitted by the hyper red LED dies.

8. The tuned LED lamp according to claim 6 wherein the plurality of LED dies comprises 7 mint LED dies, 7 hyper red LED dies, and 7 blue LED dies.

9. The tuned LED lamp according to claim 6 wherein the mint LED dies are serially connected, the hyper red LED dies are serially connected, and the blue LED dies are serially connected.

10. The tuned LED lamp according to claim 6 wherein the drive circuit is configured to deliver power to the plurality of LED dies in the ratio of:
6.9 watts to the mint LED dies, to
3.2 watts to the hyper red LED dies, to
2.0 watts to the blue LED dies.

11. The tuned LED lamp according to claim 6 wherein the drive circuit is configured to operate the plurality of LED dies to emit light having a color temperature of at least 6,200 K.

12. The tuned LED lamp according to claim 6 wherein the drive circuit is configured to operate the plurality of LED dies to emit light having a color rendering index of at least 90.

13. A tuned LED lamp comprising:
a housing;
a drive circuit disposed within the housing and configured to electrically couple to a power source; and
a plurality of LED dies mounted on a support coupled to the housing, wherein each of the plurality of LED dies is electrically coupled to and driven by the drive circuit, wherein the plurality of LED dies includes at least one blue LED die, at least one hyper red LED die and at least one mint LED die;
wherein the drive circuit is configured to operate the plurality of LED dies such that a relative peak intensity of light emitted by the at least one blue LED dies is within the range from 90% to 100% of a peak intensity of light emitted by the at least one hyper red LED dies and a relative peak intensity of light emitted by the at least one mint LED dies is within the range from 50% to 60% of the peak intensity of light emitted by the hyper red LED dies;
wherein the drive circuit is configured to operate the plurality of LED dies to emit light that selectively increases or decreases melatonin suppression in an observer of the emitted light.

14. The tuned LED lamp according to claim 13 wherein the plurality of LED dies comprises a ratio of:
15 mint LED dies, to
5 hyper red LED dies, to
4 blue LED dies; and
wherein the plurality of LED dies is serially connected.

15. The tuned LED lamp according to claim 13 wherein the drive circuit is configured to operate the plurality of LED dies to emit light having a color temperature of at least 6,200 K and a color rendering index of at least 90.

16. A tuned LED lamp comprising:
a housing;
a drive circuit disposed within the housing and configured to electrically couple to a power source; and
a plurality of LED dies mounted on a support coupled to the housing, wherein each of the plurality of LED dies is electrically coupled to and driven by the drive circuit, wherein the plurality of LED dies includes at least one blue LED die, at least one hyper red LED die and at least one mint LED die;
wherein the drive circuit is configured to operate the plurality of LED dies such that a relative peak intensity of light emitted by the blue LED dies is within the range from 80% to 90% of a peak intensity of light emitted by the hyper red LED dies and a relative peak intensity of light emitted by the mint LED is within the range from 30% to 40% of the peak intensity of light emitted by the hyper red LED dies; and
wherein the drive circuit is configured to operate the plurality of LED dies to emit light that selectively increases or decreases melatonin suppression in an observer of the emitted light.

17. The tuned LED lamp according to claim 16 wherein the plurality of LED dies comprises a ratio of:
1 mint LED die, to
1 hyper red LED die, to
1 blue LED die; and
wherein the plurality of LED dies comprises the mint LED dies are serially connected, the hyper red LED dies are serially connected, and the blue LED dies are serially connected.

18. The tune LED lamp according to claim 16 wherein the plurality of LED dies comprises 7 mint LED dies, 7 hyper red LED dies, and 7 blue LED dies.

19. The tuned LED lamp according to claim 16 wherein the drive circuit is configured to deliver power to the plurality of LED dies in the ratio of:
6.9 watts to the mint LED dies, to
3.2 watts to the hyper red LED dies, to
2.0 watts to the blue LED dies.

20. The tuned LED lamp according to claim 16 wherein the drive circuit is configured to operate the plurality of LED dies to emit light having a color temperature of at least 6,200 K and a color rendering index of at least 90.

\* \* \* \* \*